(12) United States Patent
Kang et al.

(10) Patent No.: US 8,999,698 B2
(45) Date of Patent: Apr. 7, 2015

(54) COMPETITIVE AND EFFECTIVE BACTERIAL STRAINS

(75) Inventors: Yaowei Kang, Christianburg, VA (US); Jessica Smith, Roanoke, VA (US); Shawn Semones, Salem, VA (US); Kristi Woods, Blacksburg, VA (US)

(73) Assignee: Novozymes Biologicals, Inc., Salem, VA (US)

( * ) Notice: Subject to any disclaimer, the term of this patent is extended or adjusted under 35 U.S.C. 154(b) by 104 days.

(21) Appl. No.: 13/436,268

(22) Filed: Mar. 30, 2012

(65) Prior Publication Data

US 2012/0252672 A1 Oct. 4, 2012

Related U.S. Application Data

(60) Provisional application No. 61/470,145, filed on Mar. 31, 2011, provisional application No. 61/583,413, filed on Jan. 5, 2012.

(51) Int. Cl.
| | |
|---|---|
| C12N 1/20 | (2006.01) |
| A01N 63/02 | (2006.01) |
| C12R 1/41 | (2006.01) |
| A01N 63/00 | (2006.01) |
| C05F 11/08 | (2006.01) |
| C12R 1/01 | (2006.01) |

(52) U.S. Cl.
CPC . *C12R 1/41* (2013.01); *A01N 63/00* (2013.01); *C05F 11/08* (2013.01); *C12R 1/01* (2013.01)

(58) Field of Classification Search
CPC ... A01N 63/00; A01N 2300/00; A01N 55/00; C12N 1/20; C12N 15/8274; C12N 5/0025; C12N 9/0069; A61K 8/19; A61K 8/99
USPC ........ 435/252.2, 174, 244, 252.1, 253.6, 878; 504/100, 101, 117; 424/93.1, 93.4, 424/93.46, 93.47, 93.48, 93.5, 93.51
See application file for complete search history.

(56) References Cited

U.S. PATENT DOCUMENTS

| | | | |
|---|---|---|---|
| 4,536,207 A | 8/1985 | McCandliss |
| 4,812,159 A | 3/1989 | Freepons |
| 4,886,541 A | 12/1989 | Hadwiger |
| 4,940,840 A | 7/1990 | Suslow |
| 4,964,894 A | 10/1990 | Freepons |
| 4,978,381 A | 12/1990 | Hadwiger |
| 5,026,417 A | 6/1991 | Kucey |
| 5,057,141 A | 10/1991 | Rodriquez-Kabana |
| 5,104,437 A | 4/1992 | Hadwiger |
| 5,175,149 A | 12/1992 | Stacey |
| 5,321,011 A | 6/1994 | Stacey |
| 5,374,627 A | 12/1994 | Ito |
| 5,454,464 A | 10/1995 | Yamamoto |
| 5,536,155 A | 7/1996 | Futaki |
| 5,549,718 A | 8/1996 | Lerouge |
| 5,554,445 A | 9/1996 | Struszczyk |
| 5,586,411 A | 12/1996 | Gleddie |
| 5,628,810 A | 5/1997 | Dugast |
| 5,696,098 A | 12/1997 | Muraki |
| 5,702,752 A | 12/1997 | Gugger |
| 5,705,634 A | 1/1998 | Bredehorst |
| 5,720,793 A | 2/1998 | Kato |
| 5,726,123 A | 3/1998 | Heinsohn |
| 5,733,851 A | 3/1998 | Villanueva |
| 5,830,459 A | 11/1998 | Cuero |
| 5,965,545 A | 10/1999 | Ben-Shalom |
| 5,990,291 A | 11/1999 | Waggle |
| 6,060,429 A | 5/2000 | Ben-Shalom |
| 6,146,668 A | 11/2000 | Kelly |
| 6,167,652 B1 | 1/2001 | Heinsohn |
| 6,193,988 B1 | 2/2001 | Stoner |
| 6,197,942 B1 | 3/2001 | Muraki |
| 6,200,929 B1 | 3/2001 | Horibe |
| 6,242,381 B1 | 6/2001 | van der Krieken |
| 6,258,749 B1 | 7/2001 | Nonomura |
| 6,352,727 B1 | 3/2002 | Takahashi |
| 6,407,040 B1 | 6/2002 | Nichols |
| 6,413,910 B1 | 7/2002 | Vasiljevich |
| 6,524,998 B1 | 2/2003 | Kloepper |
| 6,589,942 B1 | 7/2003 | Ben-Shalom |
| 6,606,822 B2 | 8/2003 | Bonfiglio |
| 6,649,566 B2 | 11/2003 | Doostdar |
| 6,849,576 B2 | 2/2005 | Suzuki |
| 6,878,819 B1 | 4/2005 | Natunen |

(Continued)

FOREIGN PATENT DOCUMENTS

| | | |
|---|---|---|
| EP | 1228079 B1 | 8/2004 |
| WO | 00/04778 A1 | 2/2000 |

(Continued)

OTHER PUBLICATIONS

Cytryn et al, 2007, J Bacteriology, 189(19), 6751-6762.
Deaker et al., 2007, Soil Biology & Biochemistry 39 573-580.
Denarie et al, 1996, Ann Rev Biochem 65, 503-535.
LePrince et al, 2010, Plant Science 179 554-564.
Mabood et al, 2006, Field Crops Research, 95 412-419.
Mary et al, 1994, Soil Biol Biochem 26(9), 1125-1132.
Radwan et al, 2007, Intl J Phytoremediation 9, 475-486.
Streeter, 2003, J Appl Microbiol 95, 484-491.
Sugawara et al, 2010, Appl Environ Microbiol 76(4), 1071-1081.
Supanjani et al, 2006 Plant Physiology and Biochemistry, 44 866-872.
Zahran., 2001, Journal of Biotechnology, 91 143-153.
Althabegoiti et al, 2008, FEMS Microbiol Lett 282, 115-123.
Cregan et al, 1989, Appl Environ Microbiol 55(10), 2532-2536.

(Continued)

*Primary Examiner* — Padma V Baskar
(74) *Attorney, Agent, or Firm* — Adam L. Rucker

(57) ABSTRACT

According to the present invention new isolates of bacterial strains have been shown to possess unique properties. These bacterial strains are plant growth-promoting rhizobacterium (PGPR), posses an enhanced competitive advantage at colonizing leguminous plants, and enhance the overall performance of leguminous plant growth. Further still, the present invention discloses a novel method for screening and selecting bacterial strains having the aforementioned beneficial characteristics.

21 Claims, 4 Drawing Sheets

(56) References Cited

U.S. PATENT DOCUMENTS

| | | |
|---|---|---|
| 6,933,380 B2 | 8/2005 | Huang |
| 6,979,664 B1 | 12/2005 | Smith |
| 7,250,068 B1 | 7/2007 | Smith |
| 7,262,151 B2 | 8/2007 | Smith |
| 7,576,213 B2 | 8/2009 | Flematti |
| 7,619,076 B2 | 11/2009 | Beau |
| 7,637,980 B2 | 12/2009 | Smith |
| 2005/0187107 A1 | 8/2005 | Smith |
| 2007/0027032 A1 | 2/2007 | Chen |
| 2008/0248953 A1 | 10/2008 | Smith |
| 2010/0087369 A1 | 4/2010 | Cutsem |
| 2010/0099560 A1 | 4/2010 | Hnatowich |
| 2012/0252672 A1 | 10/2012 | Kang |

FOREIGN PATENT DOCUMENTS

| | | |
|---|---|---|
| WO | 2005/062899 A2 | 7/2005 |
| WO | 2005/063784 A1 | 7/2005 |
| WO | 2008/085958 A1 | 7/2008 |
| WO | 2010/049751 A1 | 5/2010 |

OTHER PUBLICATIONS

Kaneko et al, 2011, Genes 2, 763-787.
Ravuri et al, 1992, Agronomy J 84, 1051-1056.
Santasup et al, 2000, Soil Sci Plant Nutr 46(2), 541-548.
Zhang et al, 2002, Crop Sci, 42, 1186-1190.
Zhang et al, 2003, Eur J Agronomy, 19, 205-213.
Alves, et al., 2003, Plant and Soil 252, 1-9.
Bloem, J.F., et al., 2001, Bio Fertil. Soils 33, 181-189.
Maier, et al., 1990, Appl. Environ. Microbiol. 56 (8), 2341-2346.
van der Holst et al, 2001, Curr Opin Struc Biol 11, 608-616.
Robina et al, 2002, Tetrahedron 58, 521-530.
Samain et al, 1999, J Biotechnol 72, 33-47.
Samain et al, 1997, Carb Res 302, 35-42.
Cottaz et al, 2005, Metabolic Engineering 7, 311-317.
Dumon et al, 2006, Chem Bio Chem 7, 359-365.
Denaire et al, 1996, Annu Rev Biochem 65, 503-535.
Khan et al, 2002, Photosynthetica 40(4), 621-624.
Jung et al, 2007, Carb Polymers 67, 256-259.
Yoshikawa et al, 1993, Plant Cell Physiol 34(8), 1163-1173.
Hamel et al, 2010, Planta 232, 787-806.
Okada et al, 2002, Plant Cell Physiol 43(5), 505-512.
Muller et al, 2000, Plant Physiology 124, 733-739.
Prome et al, 1998, Pure & Appl Chem, 70(1), 55-60.
Newsmart Chitosan Oligosaccharide products listing from www.glucosamine-chitosan.com webpage 2005-2008.
Darvill et al, 1992, Glycobiology 2(3), 181-198.
Cote et al, 1994, Plant Mol Biol 26, 1379-1411.
Kasprezewska 2003, Cell & Mol Biol Ltrs 8, 809-824.
Cote et al, 1995, Physiologia Plantarium 93, 41-410.
Halford 2010, Chem & Engineer News 88(15), 37-38.
D'Haez et al, 2002, Glycobiology 12(6), 79r-105r.
Demont-Caulet et al, 1999, Plant Physiology 120, 83-92.
Maillet et al, 2011, Nature 469, 58-64.
Macchiavelli et al, 2004, J Experimental Botany 55(408), 2635-2640.
Spaink 2000, Annu Rev Microbiol 54, 257-288.
Pochanavanich et al 2002, Letters Appl Microbiol 35, 17-21.
Shaw et al, 2006, Environ Microbiol 8(11), 1867-1880.
Ralston et al, 2005, Plant Physiology 137, 1375-1388.
Wakelin et al, 2004, Biol Fertil Soils 40, 36-43.
Herman et al, 2000, MPMI 13(3), 268-276.
Hungria et al, 1997, Soil Biol Biochem 29(5,6), 819-830.
Friesen et al, 2005, Appl Microbiol Biotechnol 68, 397-404.

COMPETITIVE AND EFFECTIVE BACTERIAL STRAINS

CROSS-REFERENCE TO RELATED APPLICATIONS

This application claims the benefit under 35 U.S.C. 119 of U.S. provisional application Nos. 61/470,145 and 61/583,413 filed Mar. 31, 2011 and Jan. 5, 2012, respectively, the contents of which are fully incorporated herein by reference.

REFERENCE TO SEQUENCE LISTING

This application contains a Sequence Listing in computer readable form. The computer readable form is incorporated herein by reference.

REFERENCE TO A DEPOSIT OF BIOLOGICAL MATERIAL

This application contains a reference to a deposit of biological material, which deposit is incorporated herein by reference. For complete information see Table 1.

FIELD OF THE INVENTION

The present invention relates to isolated bacterial strains, and a method of selecting bacterial strains having enhanced competitiveness and performance characteristics.

BACKGROUND OF THE INVENTION

In order to maintain healthy growth, plants must extract a variety of elements from the soil in which they grow. These elements include nitrogen and the so-called micro-nutrients (e.g., copper, iron and zinc), but many soils are deficient in such elements or they contain them only in forms which cannot be readily taken up by plants (it is generally believed that essential elements cannot be readily taken up by plants unless they are present in dissolved form in the soil). Nitrogen is an essential element for most plants as it plays a role in the synthesis of amino acids, proteins, nucleotides, nucleic acids, chlorophyll, co-enzymes and in the overall growth and health of the plant. To counteract such deficiencies, sources of the deficient elements are commonly applied to soils in order to improve growth rates and yields obtained from crop plants. For example, nitrate and/or ammonium is often added to soil to counteract a lack of available nitrogen.

In the field of crop science, it is well known that many cultivated crops require that the soil provide relatively large amounts of nitrogen to the plant. The notable exceptions to those plants requiring nitrogen via the soil are plants from the legume family.

Specifically, leguminous plants are unique from non-leguminous plants in their ability to fix atmospheric nitrogen into ammonia. The ability to fix atmospheric nitrogen into a useable nitrogen source for the plant obviates the need for the plant to obtain nitrogen from the soil. Nitrogen fixation, however, requires a symbiotic relationship between the leguminous plant and native bacterial within the soil. One of the most extensively studied partners in this symbiotic relationship is bacteria belonging to the genus *Bradyrhizobium* or *Rhizobium*. Gresshoff, P. (1999). *Identification of Plant Genes Involved in Plant-Microbe Interactions*. Stacey, G. & Keen, T. (Ed.), *Plant-Microbe Interactions* (4th ed.) (Ch. 6). St. Paul: APS Press.

Symbiosis is generally achieved through an exchange of complex bidirectional signaling between the plant and the microbe and the microbe and the plant. Typically, plant factors, such as flavonoids and flavonoid like substances, induce colonization of the bacteria into the root nodule of the leguminous plant. (Gresshoff, 1999). Once the bacteria has colonized the root nodule, the bacteria effect morphological changes in the plant, namely root hair curling and the development of a new root organ—the nodule. (Gresshoff, 1999). The nodule permits the establishment of a new physiological environment for the nodule inducing bacteria to differentiate into a nitrogen-fixing endosymbiont, or bacteriod, for the colonized plant. (Gresshoff, 1999).

It is well known that *Rhizobial* motility and chemotaxis are important attributes for strain competiveness. For example, Althabegoiti, et al., 2008, *FEMS Microbiol. Lett.* 282: 115-123 discusses deriving a spontaneous mutant strain from USDA 110 having increased motility which enhances nodulation when compared to its wild type strain. Further. Maier, et al., 1990, *Appl. Environ. Microbiol.* 56 (8): 2341-2346 discusses the role of molybdenum during the biological nitrogen fixation process. Further still, Alves, et al., 2003. Plant and Soil 252: 1-9 discusses soybean inoculants used in Brazil and the importance of competiveness for effective nitrogen fixation. Finally, Bloem, J. F., et al., 2001, *Bio Fertil. Soils* 33: 181-189 reports the importance of competitiveness in strain selection. In the study, the researchers use genetic engineering methods to put a reporter gene (GUS) into their index strain as a way to determine the competitiveness of strains. (Bloem, et al. 2001). As the study performed (Bloem, et al. 2001) required an extensive use of chemical staining and microscopy technology, the method reported remains an impractical approach for screening large samples of microbes.

It is an object of the present invention to provide a super competitive isolate(s) of bacteria from the genus *Bradyrhizobia* for colonizing leguminous plants that outperforms the colonizing ability of commercially available strains, e.g., commercial strain USDA 532C. It is a further object of the present invention to provide a super competitive isolate(s) of bacteria from the genus *Bradyrhizobia* for colonizing leguminous plants capable of enhancing the effectiveness at promoting leguminous plant growth in comparison to commercially available strains, e.g., commercial strain USDA 532C.

SUMMARY OF THE INVENTION

In order to improve the overall plant health and the availability of a usable Nitrogen source for plants, a need exists for bacterial strains which are superior at colonizing plants and enhancing overall plant growth. The isolated strains of the present invention realize these benefits.

The present invention relates to isolated strains of bacteria having at least the following enhanced characteristics in comparison to commercially available strains, e.g., commercial strain USDA 532C, wherein enhanced characteristics include, but are not limited to:
  a. enhanced competitiveness for colonizing a plant; and
  b. enhanced effectiveness at promoting plant growth.

The present invention is directed to a biologically pure culture(s) of *Bradyrhizobia japonicum* strain(s)
  the strain having the deposit accession number NRRL B-50592 (deposited also as NRRL B-59571);
  the strain having the deposit accession number NRRL B-50593 (deposited also as NRRL B-59572);
  the strain having the deposit accession number NRRL B-50586 (deposited also as NRRL B-59565);

the strain having the deposit accession number NRRL B-50588 (deposited also as NRRL B-59567);
the strain having the deposit accession number NRRL B-50587 (deposited also as NRRL B-59566);
the strain having the deposit accession number NRRL B-50589 (deposited also as NRRL B-59568);
the strain having the deposit accession number NRRL B-50591 (deposited also as NRRL B-59570);
the strain having the deposit accession number NRRL B-50590 (deposited also as NRRL B-59569);
the strain having the deposit accession number NRRL B-50594 (deposited also as NRRL B-50493);
the strain having the deposit accession number NRRL B-50726;
the strain having the deposit accession number NRRL B-50727;
the strain having the deposit accession number NRRL B-50728;
the strain having the deposit accession number NRRL 8-50729; and the strain having the deposit accession number NRRL B-50730, or a combination of at least two or more of the above deposited strains.

The present invention also relates to isolated bacterial strain(s) of the present invention includes strain(s) that are closely related to any of the above strains on the basis of 16S rDNA sequence identity, and which are at least 95% identical to any of the above strains on the basis of 16S rDNA sequence identity.

The present invention further includes a method of enhancing plant growth, comprising applying to plants, plant seeds, or soil surrounding plants, or plant seeds a composition comprising at least one of the strains of the present invention or a combination of at ieast two or more of the above deposited strains.

The invention further includes compositions comprising one or more strains of the present invention, including with an agronomically acceptable carrier.

DETAILED DESCRIPTION OF THE INVENTION

Figure 1A:
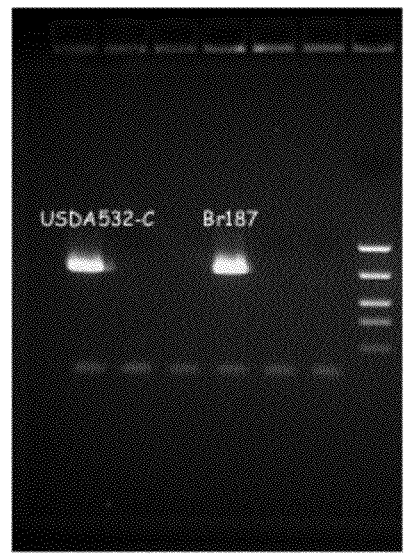
FIG. 1A is an image of a PCR gel showing a unique Primer 209 specific to USDA 532C.

The present invention provides isolated strains of bacteria having at least the following enhanced characteristics in comparison to commercially available strains, e.g., commercial strain USDA 532C, wherein enhanced characteristics include, but are not limited to:
a. enhanced competitiveness for colonizing a plant; and
b. enhanced effectiveness at promoting plant growth.

"Bacterial strain(s)" as used herein, means bacterial strains that are diazotrophs. That is, bacteria which are symbiotic nitrogen-fixing bacteria Non-limiting examples of bacterial strains as used herein include, but are not limited to bacteria from the genera *Rhizobium* spp. (e.g., *R. cellulosilyticum, R. daejeonense, R. etli, R. galegae, R. gallicum, R. giardinii, hainanense, R. huautlense, R. indigoferae, R. leguminosarum, R. loessense, R. lupini, R. lusitanum, R. mongolense, R. miluonense, R. sullae, R. tropici, R. undicola*, and/or *R. yanglingense*), *Bradyrhizobium* spp. (e.g., *B. bete, B. canariense, B. elkanii, B. iriomotense, B. japonicum, B jicamae, B. Liaoningense, B. pachyrhizi*, and/or *B. yuanmingense*), *Azorhizobium* spp. (e.g., *A. caulinodans* and/or *A. doebereineae*), *Sinorhizobium* spp. (e.g., *S. abri, S. adhaerens, S. americanum, S. aboris, S. fredii, S. indiaense, S. kostiense, S. kummerowiae, S. medicae, S. meliloti, S. mexicanus, S. morelense, S. saheli, S. terangae*, and/or *S. xinjiangense*), *Mesorhizobium* spp (*M. albiziae, M. amorphae, M. chacoense, M. ciceri, M. huakuii, M, loti, M. mediterraneum, M, pluifarium, M. septentrionale, M. temperatum, M. tianshanense*). In one particular embodiment, bacterial strain(s) of the invention further include *Bradyrhizobium japonicum* strains having the deposit accession numbers NRRL B-50592 (deposited also as NRRL B-59571), NRRL B-50593 (deposited also as NRRL B-59572), NRRL B-50586 (deposited also as NRRL B-59565), NRRL B-50588 (deposited also as NRRL B-59567), NRRL B-50587 (deposited also as NRRL B-59566), NRRL B-50589 (deposited also as NRRL B-59568), NRRL B-50591 (deposited also as NRRL B-59570), NRRL B-50590 (deposited also as NRRL B-59569), NRRL B-50594 (deposited also as NRRL B-50493); NRRL B-50726; NRRL B-50727; NRRL B-50728; NRRL B-50729; NRRL B-50730, or a combination of at least two or more of the above deposited strains, including two of the above strains, at least three of the above strains, at least four of the above strains, at least five of the above strains, at least six of the above strains, at least seven of the above strains, at least eight of the above strains, at least nine of the above strains, at least ten of the above strains, at least eleven of the above strains, at least twelve of the above strains, at least thirteen of the above strains, up to and including all of the above strains.

The term "commercially available strain(s)" means commercially available bacterial strains, e.g., USDA 532C, USDA 110, USDA 123, USDA 127, USDA 129, etc. Cregan. P. B., et al., 1989, *Appl. and Enviro. Microbiol.* 55 (10): 2532-2536.

As used herein, "enhanced competitiveness" and/or "enhanced nodulation" is defined to mean bacterial strain(s) possessing a dominant percent nodule occupancy, e.g. at least 50%, at least 55%, at least 60%, at least 65%, at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, up to 100% nodule occupancy, "Enhanced competitiveness" was determined pursuant to the detailed assay(s) described below (see Materials and Methods: "Primary Screening Protocol" and "Competition Study Protocol").

As used herein, the term "nodule" is defined to include, but is not intended to be limited to, determinate nodules, indeterminate nodules, or a combination thereof. Examples of determinate nodules and indeterminate nodules are well known in the art and described in Denison, R. F., 2000, *The Amer. Naturalist.* 156 (6): 567-576. Determinate nodules are found on *Glycine, Lotus*, or *Phaseolus* species and are round and spherical in shape. (Denison, 2000) Determinate nodules grow only for a limited period of time—typically a few weeks. (Denison, 2000) In contrast to determinate nodules, indeterminate nodules are found on *Medicago, Trifolium*, and *Pisium* species, have an elongated shape and grow continuously. (Denison, 2000)

"Nodule occupancy" is a term known in the art. McDermott T. R. & Graham, P. H., *Appl. and Environ. Microbiol.* 55(10): 2493-2498. As used herein, "nodule occupancy" means the percent of nodules occupied by a bacterial strain(s) other than a commercially available *Bradyrhizobium* strain, e.g. USDA 532C, and/or the number of nodules containing a particular bacterial strain(s) other than a commercially available *Bradyrhizobium* strain, e.g. USDA 532C, divided by the total number of nodules containing all bacterial strains. "Nodule occupancy" was determined pursuant to the detailed assay(s) described below (see Materials and Methods: "Primary Screening Protocol" and "Competition Study Protocol") and can be determined from an analysis of nodules from plants obtained from either greenhouse or field samples. By way of example, percent nodule occupancy=A/(A+B) wherein A is the number of nodules containing a particular bacterial strain(s) other than a commercially available *Bradyrhizobium* strain, e.g. USDA 532C, and B is the number of nodules containing a commercially available *Bradyrhizobium* strain, e.g., USDA 532C. It is well known in the art that, notwithstanding the rare exception, a single nodule will contain only one bacterial strain. Johnston, A. W. B., et al., 1974, *J. Gen. Microhiol* 87: 343-350; Dunham, D. H. & Baldwin, I. L., 1931, *Soil Science* 32: 235-249; Johnson, H. W., et al., 1963, *Agrono, J.* 55: 269-271; Dudman, W. F. & Brockwell, J., 1968, *J. Agricul. Res.* 19: 739-747; Nicol, H. & Thorton, H. G., 1941, *Proc. Roy. Soc. B* 130, 32-59; Hughes, D. Q., & Vincent, J. M., 1942, *Proc. of the Linnenan Soc. of New South Wales* 67: 142-152; and Vincent, J. M. & Waters, L. M., 1953, *J. Gen. Microbiol.* 9: 357-370.

As used herein, "enhanced effectiveness at promoting growth" includes at least one of increased plant yield measured in terms of bushels/acre, increased fruit number, increased root number, increased root length, increased root mass, increased root volume, increased leaf area, increased plant stand, increased plant vigour, and/or increased nitrogen ($N_2$) fixing capability. "Enhanced effectiveness at promoting growth" was determined pursuant to the detailed assay(s) described below (see Materials and Methods: "Primary Screening Protocol" and "Performance Study Protocol") and can be determined from an analysis of plants obtained from either greenhouse or field samples.

As used herein "increased fruit number" means an increased total number of soybean pods on a soybean plant and/or an increased total dry weight of soybean pods on a soybean plant.

As used herein "total dry weight" means the weight of plant matter (e.g., plant fruit, plant pods, plant roots, plant nodules, whole plants, partial plants, etc.) following incubation at 80° C. for a specified period of time, e.g., at least 4 hours, at least 8 hours, at least 12 hours, at least 24 hours, at least 48 hours, etc., or any period of time necessary to dry the plant matter. It is to be understood that drying times for the purposes of determining "total dry weight" are dependent on many factors. Non-limiting factors which may impact drying time include the material to be dried, the mass of the material to be dried, the amount of material to be dried, and/or combinations thereof. Incubation can be performed in any temperature controlled device used in the art. For the purposes of this invention, "total dry weight" was determined with an Eppendorf Innova® 42R incubator.

The term "increased nitrogen ($N_2$) fixing capability," as used herein, means the isolated bacteria may increase nitrogen ($N_2$) fixation. Pursuant to the "Performance Study Protocol" provided infra (Materials and Methods), the relative nitrogen ($N_2$) fixing capability of bacteria can be quantified by measuring the total nitrogen content of the plant using standard nitrogen quantifying methods known to those possessing an ordinary skill in the art (e.g., the Kjeldahl method, etc.). See Takahashi, M., et al., 2007. Uptake, Assimilation, and Novel Metabolism of Nitrogen Dioxide in Plants, p. 109-118. In Willey (ed.), *Phytoremediation: Methods and Reviews*, vol. 23. Humana Press, New York; Bremner, M. 1965. Total nitrogen, p. 1149-1178. In C. A. Black (ed.), *Methods of soil analysis*, vol. 2. American Society for Agronomy, Madison; Schank, S. C., et al., 1981, *App. and Enviro. Microbiol.*, 41 (2): 342-345.

In yet another aspect of the present invention, the isolated bacterial strain(s) have an enhanced temperature tolerance. "Enhanced temperature tolerance" means the range of temperatures at which the isolated bacterial strain(s) are able to grow, e.g., the maximum and minimum temperatures at which isolated *Bradyrhizobium* strain(s) can grow. In one aspect, "enhanced temperature tolerance" was determined according to the "Temperature Profile Protocol" discussed infra (Materials and Methods).

In yet another aspect of the present invention, the isolated bacterial strain(s) are naturally resistant to glyphosate. In one aspect, "enhanced temperature tolerance" was determined according to the "Glyphosate Resistance Profile Protocol" discussed infra (Materials and Methods).

In another aspect, the isolated bacterial strain(s) of the present invention includes strain(s) that are closely related to any of the above strains on the basis of 16S rDNA sequence identity. See Stackebrandt E, et al., "Report of the ad hoc committee for the re-evaluation of the species definition in bacteriology," *Int J Syst Evol Microbiol.* 52(3):1043-7 (2002) regarding use of 16S rDNA sequence identity for determining relatedness in bacteria. In an embodiment, the at least one strain is at least 95% identical to any of the above strains on the basis of 16S rDNA sequence identity, at least 96% identical to any of the above strains on the basis of 16S rDNA sequence identity, at least 97% identical to any of the above strains on the basis of 16S rDNA sequence identity, at least 98% to any of the above strains on the basis of 16S rDNA sequence identity, at least 98.5% identical to any of the above strains on the basis of 16S rDNA sequence identity, at least 99% identical to any of the above strains on the basis of 16S rDNA sequence identity or at least 99.5% to any of the above strains on the basis of 16S rDNA sequence identity.

In another embodiment, the present invention includes a method for isolating bacterial strain(s) having enhanced competitiveness for occupying the nodules of a leguminous plant and enhanced effectiveness at promoting leguminous plant growth. As used herein, the term "isolate, isolates, isolating, and/or isolated, etc." means that the referenced material is removed from the environment in which it is normally found. The method includes, among other things, a. obtaining a bacterial strain(s) from a soil sample;
b. subjecting the bacterial strain(s) and a commercially available strain to a leguminous plant;
c. selecting the bacterial strain(s) which are more competitive than the commercially available strain for occupying the nodules of a leguminous plant:
d. analyzing the selected bacterial strain(s) which are more competitive than the commercially available strain for occupying the nodules of a leguminous plant for those bacterial strain(s) having an enhanced effectiveness at promoting leguminous plant growth; and
e. isolating the bacterial strain(s) having enhanced effectiveness effectiveness at promoting leguminous plant growth.

In one aspect, the isolated bacterial strain(s) are strains from the genus *Bradyrhizobium*. In still yet another aspect, the method further includes the step of screening the *Bradyrhizobium* strain(s) against a specific primer unique to a commercially available strain of *Bradyrhizobia*, e.g., commercial strain USDA 532C.

In yet another aspect, the method includes isolating a culture of *Bradyrhizobia japonicum* selected from the group consisting of:

the strain having the deposit accession number NRRL B-50592 (deposited also as NRRL B-59571);
the strain having the deposit accession number NRRL B-50593 (deposited also as NRRL B-59572);
the strain having the deposit accession number NRRL B-50586 (deposited also as NRRL B-59565);
the strain having the deposit accession number NRRL B-50588 (deposited also as NRRL B-59567);
the strain having the deposit accession NRRL B-50587 (deposited also as NRRL B-59566);
the strain having the deposit accession number NRRL B-50589 (deposited also as NRRL B-59568);
the strain having the deposit accession number NRRL B-50591 (deposited also as NRRL B-59570);
the strain having the deposit accession number NRRL B-50590 (deposited also as NRRL B-59569);
the strain having the deposit accession number NRRL B-50594 (deposited also as NRRL B-50493);
the strain having the deposit accession number NRRL B-50726;
the strain having the deposit accession number NRRL B-50727;
the strain having the deposit accession number NRRL B-50728;
the strain having the deposit accession number NRRL B-50729; and
the strain having the deposit accession number NRRL B-50730, or a combination of at least two or more of the above deposited strains, including more than two, such as, at least three of the above strains, at least four of the above strains, at least five of the above strains, at least six of the above strains, at least seven of the above strains, at least eight of the above strains, at least nine of the above strains, at least ten of the above strains, at least eleven of the above strains, at least twelve of the above strains, at least thirteen of the above strains, up to an including all of the above strains.

In still another aspect, the method includes isolating bacterial strain(s) having enhanced temperature tolerance. See Materials and Methods: "Temperature Profile Protocol."

Further still, the method includes isolating a bacterial strain(s) having natural resistance to glyphosate. See Materials and Methods: "Glyphosate Resistance Profile Protocol."

In another preferred aspect, the method includes isolating bacterial strain(s) selected from the genus consisting of *Rhizobium* and *Bradyrhizobium* capable of enhancing the nodulation of a leguminous plant.

Composition

The present invention includes a composition comprising at least one of the isolated bacterial strain(s) of the present invention or a combination of at least two or more of the above deposited strains, including more than two, such as, at least three of the above strains, at least four of the above strains, at least five of the above strains, at least six of the above strains, at least seven of the above strains, at least eight of the above strains, at least nine of the above strains, at least ten of the above strains, at least eleven of the above strains, at least twelve of the above strains, at least thirteen of the above strains, up to an including all of the above strains and an agronomically suitable carrier.

In some embodiments, the composition may be an inoculant composition. As used herein and in the art, the term "inoculant composition" refers generally to compositions or materials that introduce compatible bacterial strains either onto an external surface of seeds or in the seed furrow.

The composition may comprise one or more agronomically acceptable carriers. In instances where multiple agronomically acceptable carriers are used, the agronomically acceptable carriers may be the same or different. As used herein in connection with "carrier", the term "agronomically acceptable" refers to any material which can be used to deliver the actives to a seed, soil or plant, and preferably which carrier can be added (t) the seed, soil or plant) without having an adverse effect on plant growth, soil structure, soil drainage or the like. Suitable carriers comprise, but are not limited to, wheat chaff, bran, ground wheat straw, peat-based powders or granules, gypsum-based granules, and clays (e.g., kaolin, bentonite, montmorillonite). Formulations as liquid, peat, or wettable powder will be suitable for coating of seeds. When used to coat seeds, the material can be mixed with water, applied to the seeds and allowed to dry. Example of yet other carriers include moistened bran, dried, sieved and applied to seeds prior coated with an adhesive, e.g., gum arabic. In embodiments that entail formulation of the actives, the agronomically acceptable carrier may be aqueous. If a liquid carrier is used, the liquid (e.g., water) carrier will typically include growth media to culture the bacterial strains. Non-limiting examples of suitable growth media for the bacterial strains include mannitol yeast extract, glycerol yeast extract, or any media known to those skilled in the art to be compatible with, and/or provide growth nutrients to the bacterial strains.

Also encompassed by the compositions of the present invention are compositions including one or more signal molecules. Non-limiting examples of plant signal molecules include nod factors (i.e., lipo-chitooligosaccharies), chitooligosaccharides, chitinous compounds, flavonoids, jasmonic acid or derivatives thereof, linoleic acid or derivatives thereof, linolenic acid or derivatives thereof, karrikins, or combinations thereof.

Lipo-chitooligosaccharide compounds (LCO's), also known in the art as symbiotic Nod signals or Nod factors, consist of an oligosaccharide backbone of β-1,4-linked N-acetyl-D-glucosamine ("GlcNAc") residues with an N-linked fatty acyl chain condensed at the non-reducing end. LCO's differ in the number of GlcNAc residues in the backbone, in the length and degree of saturation of the fatty acyl chain, and in the substitutions of reducing and non-reducing sugar residues. An example of an LCO is presented below as formula I:

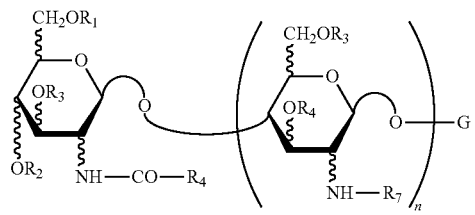

in which:

G is a hexosamine which can be substituted, for example, by an acetyl group on the nitrogen, a sulfate group, an acetyl group and/or an ether group on an oxygen, $R_1$, $R_2$, $R_3$, $R_5$, $R_6$ and $R_7$, which may be identical or different, represent H, $CH_3 CO$—, $C_x H_y CO$— where x is an integer between 0 and 17, and y is an integer between 1 and 35, or any other acyl group such as for example a carbamyl, $R_4$ represents a mono-, di- or triunsaturated aliphatic chain containing at least 12 carbon atoms, and n is an integer between 1 and 4.

LCOs may be obtained (isolated and/or purified) from bacteria such as Rhizobia, e.g., Rhizobium spp., Bradyrhizobium spp., Sinorhizobium spp. and Azorhizobium spp. LCO structure is characteristic for each such bacterial species, and each strain may produce multiple LCO's with different structures. For example, specific LCOs from S. meliloti have also been described in U.S. Pat. No. 5,549,718 as having the formula II:

LCOs from Bradyrhizobium japonicum are described in U.S. Pat. Nos. 5,175,149 and 5,321,011. Broadly, they are pentasaccharide phytohormones comprising methylfucose. A number of these B. japonicum-derived LCOs are described: BjNod-V ($C_{18:1}$); BjNod-V ($A_C$, $C_{18:1}$), BjNod-V ($C_{16:1}$); and BjNod-V ($A_c$, $C_{16:0}$), with "V" indicating the presence of five N-acetylglucosamines; "Ac" an acetylation; the number following the "C" indicating the number of carbons in the fatty acid side chain; and the number following the ":" the number of double bonds.

LCO's used in compositions of the invention may be obtained (i.e., isolated and/or purified) from bacterial strains that produce LCO's, such as strains of Azorhizobium, Bradyrhizobium (including B. japonicum), Mesorhizobium, Rhizobium (including R. leguminosarum), Sinorhizobium (including S. meliloti), and bacterial strains genetically engineered to produce LCO's.

Also encompassed by the present invention are compositions using LCOs obtained (i.e., isolated and/or purified) from a mycorrhizal fungus, such as fungi of the group Glomerocycota, e.g., Glomus infraradicus. The structures of representative LCOs obtained from these fungi are described in WO 2010/049751 and WO 2010/049751 (the LCOs described therein also referred to as "Myc factors").

Further encompassed by compositions of the present invention is use of synthetic LCO compounds, such as those described in WO 2005/063784, and recombinant LCO's produced through genetic engineering. The basic, naturally occurring LCO structure may contain modifications or substitutions found in naturally occurring LCO's, such as those described in Spaink, Crit. Rev. Plant Sci. 54:257-288 (2000) and D'Haeze., et al., Glycobiology 12:79R-105R (2002). Precursor oligosaccharide molecules (COs, which as described below, are also useful as plant signal molecules in the present invention) for the construction of LCOs may also be synthesized by genetically engineered organisms, e.g., as in Samain, et al., Carb. Res. 302:35-42 (1997); Samain, et al., J. Biotechnol. 72:33-47 (1999).

LCO's may be utilized in various forms of purity and may be used alone or in the form of a culture of LCO-producing

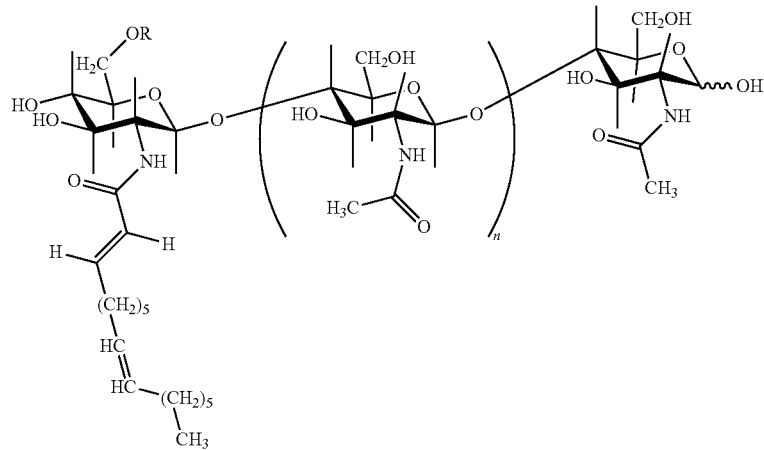

in which R represents H or $CH_3CO$— and n is equal to 2 or 3.

Even more specific LCOs include NodRM, NodRM-1, NodRM-3. When acetylated (the R=$CH_3 CO$—), they become AcNodRM-1, and AcNodRM-3, respectively (U.S. Pat. No. 5,545,718).

bacteria or fungi. Methods to provide substantially pure LCO's include simply removing the microbial cells from a mixture of LCOs and the microbe, or continuing to isolate and purify the LCO molecules through LCO solvent phase separation followed by HPLC chromatography as described, for example, in U.S. Pat. No. 5,549,718. Purification can be enhanced by repeated HPLC, and the purified LCO molecules can be freeze-dried for long-term storage.

Chitooligosaccharides (COs) are known in the art as β-1-4 linked N actyl glucosamine structures identified as chitin oligomers, also as N-acetylchitooligosaccharides. CO's have unique and different side chain decorations which make them different from chitin molecules [($C_8H_{13}NO_5$)n, CAS No. 1398-61-4], and chitosan molecules [($C_5H_{11}NO_4$)n, CAS No. 9012-76-4]. Representative literature describing the structure and production of COs is as follows: Van der Holst, et al., Current Opinion in Structural Biology, 11:608-616 (2001); Robina, et al., Tetrahedron 58:521-530 (2002); Hanel, et al., Planta 232:787-806 (2010); Rouge, et al, Chapter 27, "The Molecular Immunology of Complex Carbohydrates" in Advances in Experimental Medicine and Biology, Springer Science; Wan, el al., Plant Cell 21:1053-69 (2009); PCT/F100/00803 (9/21/2000); and Demont-Caulet, et al., Plant Physiol, 120(1):83-92 (1999). The COs may be synthetic or recombinant. Methods for preparation of recombinant COs are known in the art. See, e.g., Samain. et al. (supra.); Cottaz, et al., Meth. Eng. 7(4):311-7 (2005) and Samain, et al., J. Biotechnol. 72:33-47 (1999).

Compositions of the present invention may also include chitinous compounds (other than COs), flavonoids, jasmonic acid, linaleic acid and linolenic acid and their derivatives, and karrikins.

Chitins and chitosans, which are major components of the cell walls of fungi and the exoskeletons of insects and crustaceans, are also composed of GlcNAc residues. Chitinous compounds include chitin, (IUPAC: N-[5-[[3-acetylamino-4, 5-dihydroxy-6-(hydroxymethyl)oxan-2yl]methoxymethyl]-2-[[5-acetylamino-4,6-dihydroxy-2-(hydroxy methyl)oxan-3-yl]methoxymethyl]-4-hydroxy-6-(hydroxymethyl)oxan-3-ys]ethanamide), and chitosan, (IUPAC: 5-amino-6-[5-amino-6-[5-amino-4,6-dihydroxy-2(hydroxymethyl)oxane-3-yl]oxy-4-hydroxy-2-(hydroxymethyl)oxan-3-yl]oxy-2 (hydroxymethyl)oxane,-3,4-diol). These compounds may be obtained commercially, e.g., from Sigma-Aldrich, or prepared from insects, crustacean shells, or fungal cell walls. Methods for the preparation of chitin and chitosan are known in the art, and have been described, for example, in U.S. Pat. No. 4,536,207 (preparation from crustacean shells). Pochanavanich, et al., Lett. Appl. Microbiol. 35:17-21 (2002) (preparation from fungal cell walls), and U.S. Pat. No. 5,965, 545 (preparation from crab shells and hydrolysis of commercial chitosan). Deacetylated chitins and chitosans may be obtained that range from less than 35% to greater than 90% deacetylation, and cover a broad spectrum of molecular weights, e.g., low molecular weight chitosan oligomers of less than 15 kD and chitin oligomers of 0.5 to 2 kD; "practical grade" chitosan with a molecular weight of about 15 kD; and high molecular weight chitosan of up to 70 kD. Chitin and chitosan compositions formulated for seed treatment are also commercially available. Commercial products include, for example, ELEXA® (Plant Defense Boosters, Inc.) and BEYOND™ (Agrihouse, Inc.).

Flavonoids are phenolic compounds having the general structure of two aromatic rings connected by a three-carbon bridge. Flavonoids are produced by plants and have many functions, e.g., as beneficial signaling molecules, and as protection against insects, animals, fungi and bacteria. Classes of flavonoids include chalcones, anthocyandins, coumarins, flavones, flavanols, flavonols, flavanones, and isoflavones. See. Jain, et al., J. Plant Biochem. & Biotechnol. 11:1-10 (2002); Shaw, et al., Environmental Microbiol. 11:1867-80 (2006).

Representative flavonoids that may be useful in compositions of the present invention include genistein, daidzein, formononetin, naringenin, hesperetin, luteolin, and apigenin. Flavonoid compounds are commercially available, e.g., from Natland International Corp., Research Triangle Park, N.C.; MP Biomedicals, Irvine, Calif.; LC Laboratories, Woburn Mass. Flavonoid compounds may be isolated from plants or seeds, e.g., as described in U.S. Pat. Nos. 5,702,752; 5,990, 291; and 6,146,668. Flavonoid compounds may also be produced by genetically engineered organisms, such as yeast, as described in Ralston, at al., Plant Physiology 137:1375-88 (2005).

Jasmonic acid (JA, [1R-[1α,2β(Z)]]-3-oxo-2-(pentenyl) cyclopentaneacetic acid) and its derivatives, linoleic acid ((Z, Z)-9,12-Octadecadienoic acid) and its derivatives, and linolenic acid ((Z,Z,Z)-9,12,15-octadecatrienoic acid) and its derivatives, may also be used in compositions of the present invention. Jasmonic acid and its methyl ester, methyl jasrnonate (MeJA), collectively known as jasmonates, are octadecanoid-based compounds that occur naturally in plants. Jasmonic acid is produced by the roots of wheat seedlings, and by fungal microorganisms such as *Botryodiplodia theobromae* and *Gibbrella fujikuroi*, yeast (*Saccharomyces cerevisiae*), and pathogenic and non-pathogenic strains of *Escherichia coli*. Linoleic acid and linolenic acid are produced in the course of the biosynthesis of jasmonic acid. Jasmonates, linoleic acid and linoleic acid (and their derivatives) are reported to be inducers of nod gene expression or LCO production by rhizobacteria. See, e.g., Mabood, Fazli, Jasmonates induce the expression of nod genes in *Bradyrhizobium japonicum*, May 17, 2001; and Mabood, Fazli, "Linoleic and linolenic acid induce the expression of nod genes in *Bradyrhizobium japonicum*," USDA 3, May 17, 2001.

Useful derivatives of linoleic acid, linolenic acid, and jasmonic acid that may be useful in compositions of the present invention include esters, amides, glycosides and salts. Representative esters are compounds in which the carboxyl group of linoleic acid, linolenic acid, or jasmonic acid has been replaced with a —COR group, where R is an —OR$^1$ group, in which R$^1$ is: an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example. N, O, P, or S. Representative amides are compounds in which the carboxyl group of linoleic acid, linolenic acid, or jasmanic acid has been replaced with a —COR group, where R is an NR$^2$R$^3$ group, in which R$^2$ and R$^3$ are independently; hydrogen; an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example. N, O, P, or S. Esters may be prepared by known methods, such as acid-catalyzed nucleophilic addition, wherein the carboxylic acid is reacted with an alcohol in the presence of a catalytic amount of a mineral acid. Amides may also be prepared by known methods, such as by reacting the carboxylic acid with the appropriate amine in the presence of a coupling agent such as dicyclohexyl carbodiimide (DCC), under neutral conditions. Suitable salts of linoleic acid, linolenic acid, and jasmonic acid include e.g., base addition salts. The bases that may be used as reagents to prepare metabolically acceptable base salts of these compounds include those derived from cations such as alkali metal cations (e.g., potassium and sodium) and alkaline earth metal cations (e.g., calcium and magnesium). These salts may be readily prepared by mixing together a solution of linoleic acid, linolenic acid, or jasmonic acid with a solution of the base. The salt may be precipitated from solution and be collected by filtration or may be recovered by other means such as by evaporation of the solvent.

Karrikins are vinylogous 4H-pyrones e.g., 2H-furo[2,3-c] pyran-2-ones including derivatives and analogues thereof. Examples of these compounds are represented by the following structure:

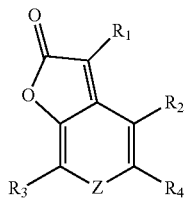

wherein; Z is O, S or $NR_5$; $R_1$, $R_2$, $R_3$, and $R_4$ are each independently H, alkyl, alkenyl, alkynyl, phenyl, benzyl, hydroxy, hydroxyalkyl, alkoxy, phenyloxy, benzyloxy, CN, $COR_6$, COOR=, halogen, $NR_6R_7$, or $NO_2$; and $R_5$, $R_6$, and $R_7$ are each independently H, alkyl or alkenyl, or a biologically acceptable salt thereof. Examples of biologically acceptable salts of these compounds may include acid addition salts formed with biologically acceptable acids, examples of which include hydrochloride, hydrobromide, sulphate or bisulphate, phosphate or hydrogen phosphate, acetate, benzoate, succinate, fumarate, maleate, lactate, citrate, tartrate, gluconate; methanesulphonate, benzenesulphonate and p-toluenesulphonic acid. Additional biologically acceptable metal salts may include alkali metal salts, with bases, examples of which include the sodium and potassium salts. Examples of compounds embraced by the structure and which may be suitable for use in the present invention include the following: 3-methyl-2H-furo[2,3-c]pyran-2-one (where $R_1$=$CH_3$, $R_2$, $R_3$, $R_4$=H), 2H-furo[2,3-c]pyran-2-one (where $R_1$, $R_2$, $R_3$, R4=H), 7-methyl-2H-furo[2,3-c]pyran-2-one (where $R_1$, $R_2$, $R_4$=H, $R_3$=$CH_3$), 5-methyl-2H-furo[2,3-c] pyran-2-one (where $R_1$, $R_2$, $R_3$=H, $R_4$=$CH_3$), 3,7-dimethyl-2H-furo[2,3-c]pyran-2-one (where $R_1$, $R_3$=$CH_3$, $R_2$, $R_4$=H), 3,5-dimethyl-2H-furo[2,3-c]pyran-2-one (where $R_1$, $R_4$=$CH_3$, $R_2$, $R_3$=H), 3,5,7-trimethyl-2H-furo[2,3-c]pyran-2-one (where $R_1$, $R_3$, $R_4$=$CH_3$, $R_2$=H), 5-methoxymethyl-3-methyl-2H-furo[2,3-c]pyran-2-one (where $R_1$=$CH_3$, $R_2$, $R_3$=H, $R_4$=$CH_2OCH_3$), 4-bromo-3,7-dimethyl-2H-furo[2,3-c]pyran-2-one (where $R_1$, $R_3$=$Ch_3$, $R_2$=Br, $R_4$=H), 3-methyl-furo[2,3-c]pyridin-2(3H)-one (where Z=NH, $R_1$=$CH_3$, $R_2$, $R_3$, $R_4$=H), 3,6-dimethylfuro[2,3-c]pyridin-2(6H)-one (where Z=N—$CH_3$, $R_1$=$CH_3$, $R_2$, $R_3$, $R_4$=H). See, U.S. Pat. No. 7,576,213. These molecules are also known as karrikins. See, Halford. supra.

Compositions of the present invention may further include an agriculturally/agronomically beneficial agent, Non-limiting examples of such agents that may be useful in the practice of the present invention include herbicides, fungicides and insecticides.

Suitable herbicides include bentazon, acifluorfen, chlorimuron, lactofen, clomazone, fluazifop, glufosinate, glyphosate, sethoxydim, imazethapyr, imazamox, fomesafe, flumiclorac, imazaquin, and clethodim. Commercial products containing each of these compounds are readily available. Herbicide concentration in the composition will generally correspond to the labeled use rate for a particular herbicide.

A "fungicide" as used herein and in the art, is an agent that kills or inhibits fungal growth. As used herein, a fungicide "exhibits activity against" a particular species of fungi if treatment with the fungicide results in killing or growth inhibition of a fungal population (e.g., in the soil) relative to an untreated population. Effective fungicides in accordance with the invention will suitably exhibit activity against a broad range of pathogens, including but not limited to *Phytophthora*, *Rhizoctonia*, *Fusarium*, *Pythium*, *Phomopsis* or *Selerotinia* and *Phakopsora* and combinations thereof.

Commercial fungicides may be suitable for use in the present invention. Suitable commercially available fungicides include PROTÉGÉ. RIVAL or ALLEGIANCE FL or LS (Gustafson, Plano, Tex.), WARDEN RTA (Agrilance, St. Paul, Minn.), APRON XL, APRON MAXX RTA or RFC, MAXIM 4FS or XL (Syngenta, Wilmington, Del.), CAFTAN (Arvesta, Guelph, Ontario) and PROTREAT (Nitragin Argentina, Buenos Ares, Argentina). Active ingredients in these and other commercial fungicides include, but are not limited to, fludioxonil, mefenoxam, azoxystrobin and metalaxyl. Commercial fungicides are most suitably used in accordance with the manufacturer's instructions at the recommended concentrations.

As used herein, an insecticide "exhibits activity against" a particular species of insect if treatment with the insecticide results in killing or inhibition of an insect population relative to an untreated population. Effective insecticides in accordance with the invention will suitably exhibit activity against a broad range of insects including, but not limited to, wireworms, cutworms, grubs, corn rootworm, seed corn maggots, flea beetles, chinch bugs, aphids, leaf beetles, and stink bugs.

Commercial insecticides may be suitable for use in the present invention. Suitable commercially-available insecticides include CRUISER (Syngenta, Wilmington, Del.), GAUCHO and PONCHO (Gustafson, Plano, Tex.). Active ingredients in these and other commercial insecticides include thiamethoxam, clothianidin, and imidacloprid. Commercial insecticides are most suitably used in accordance with the manufacturer's instructions at the recommended concentrations.

Compositions of the present invention also are intended to include the use of one or more phosphate solubilizing agent. As used herein, phosphate solubilizing agents, include, but are not limited to, phosphate solubilizing microorganisms. As used herein, "phosphate solubilizing microorganism" is a microorganism that is able to increase the amount of phosphorous available for a plant. Phosphate solubilizing microorganisms include fungal and bacterial strains. In an embodiment, the phosphate solubilizing microorganism is a spore forming microorganism.

Non-limiting examples of phosphate solubilizing microorganisms include species from a genus selected from the group consisting of *Acinetobacter*, *Arthrobacter*, *Arthrobotrys*, *Aspergillus*, *Azospirillum*, *Bacillus*, *Burkholderia*, *Candida Chryseornonas*, *Enterobacter*, *Eupenicillium*, *Exiguobacterium*, *Klebsiella*, *Kluyvera*, *Microbacterium*, *Mucor*, *Paecilomyces*, *Paenibacillus*, *Penicillium*, *Pseudomonas*, *Serratia*, *Stenotrophomonas*, *Streptomyces*, *Streptosporangium*, *Swaminathania*, *Thiobacillus*, *Torulospora*, *Vibrio*, *Xanthobacter*, and *Xanthomonas*.

Non-limiting examples of phosphate solubilizing microorganisms are selected from the group consisting *Acinetobacter calcoaceticus*, *Acinetobacter* spp., *Arthrobacter* spp., *Arthrobotrys oligospora*, *Aspergillus niger*, *Aspergillus* spp.,

*Azospirillum halopraeferans, Bacillus amyloliquefaciens, Bacillus atrophaeus, Bacillus circulans, Bacillus licheniformis, Bacillus subtilis, Burkholderia cepacia, Burkholderia vietnamiensis, Candida krissii, Chryseomonas luteola, Enterobacter aerogenes, Enterobacter asburiae, Enterobacter* spp., *Enterobacter taylorae, Eupenicillium parvum, Exiguobacterium* spp., *Klebsiella* spp., *Kluyvera cryocrescens, Microbacterium* spp., *Mucor ramosissimus, Paecilomyces hepialid, Paecilomyces marquandii, Paenibacillus macerans, Paenibacillus mucilaginosus, Pantoea aglomerans, Penicillium expansum, Pseudomonas corrugate, Pseudomonas fluorescens, Pseudomonas lutea, Pseudomonas poae, Pseudomonas putida, Pseudomonas stutzeri, Pseudomonas trivialis, Serratia marcescens, Stenotrophomonas maltophilia, Streptomyces* sp., *Streptosporangium* spp., *Swaminathania salitolerans, Thiobacillus ferrooxidans, Torulospora globosa, Vibrio proteolyticus, Xanthobacter agilis,* and *Xanthomonas campestris.*

In one embodiment, the phosphate solubilizing microorganism is a strain of the fungus *Penicillium*. Strains of the fungus *Penicillium* that may be useful in the practice of the present invention include *P. bilaiae* (formerly known as *P. bilaii), P. albidum, P. aurantiogriseum, P. chrysogenum, P. citreonigrum, P. citrinum, P. digitatum, P. frequentas, P. fuscum, P. gaestrivorus, P. glabrum, P. griseofulvum, P. implicatum, P. janthinellum, P. lilacinum, P. miniolutem, P. montanense, P. nigricans, P. oxalicum, P. pinetorum, P. pinophilum, P. purpurogenum, P. radicans, P. radicum, P. raistrickii, P. rugulosum, P. simplicissimum, P. solitum, P. variabile, P. velutinum, P. viridicatum, P. glaucum, P. fussiporus,* and *P. expansum.*

In another embodiment, the phosphate solubilizing microorganism *Penicillium* species is *P. bilaiae, P. gaestrivorus,* and/or a combination thereof. In still another embodiment, the *P. bilaiae* strains are selected from the group consisting of ATCC 20851, NRRL 50169, ATCC 22348, ATCC 18309, NRRL 50162 (Wakelin, et al., 2004. Biol Fertil Soils 40:36-43) and the *P. gaestrivorus* strain is NRRL 50170 (see, Wakelin, supra.).

According to compositions of the invention, it is envisioned that more than one phosphate solubilizing microorganism may be used, such as, at least two, at least three, at least four, at least five, at least 6, including any combination of the *Acinetobacter, Arthrobacter, Arthrobotrys, Aspergillus, Azospirillum, Bacillus, Burkholderia, Candida Chryseomonas, Enterobacter, Eupenicillium, Exiguobacterium, Klebsiella, Kluyvera, Microbacterium, Mucor, Paecilomyces, Paenibacillus, Penicillium, Pseudomonas, Serratia, Stenotrophomonas, Streptomyces, Streptosporangium, Swaminathania, Thiobacillus, Torulospora, Vibrio, Xanthobacter,* and *Xanthomonas*, including one species selected from the following group: *Acinetobacter calcoaceticus, Acinetobacter* spp., *Arthrobacter* spp. *Arthrobotrys oligospora, Aspergillus niger, Aspergillus* spp., *Azospirillum halopraeferans, Bacillus amyloliquefaciens, Bacillus atrophaeus, Bacillus circulans, Bacillus licheniformis, Bacillus subtilis, Burkholderia cepacia, Burkholderia vietnamiensis, Candida krissii, Chryseomonas luteola, Enterobacter aerogenes, Enterobacter asburiae, Enterobacter* spp., *Enterobacter taylorae, Eupenicillium parvum, Exiguobacterium* spp., *Klebsiella* spp., *Kluyvera cryocrescens, Microbacterium* spp., *Mucor ramosissimus, Paecilomyces hepialid, Paecilomyces marquandii, Paenibacillus macerans, Paenibacillus mucilaginosus, Pantoea aglomerans, Penicillium expansum, Pseudomonas corrugate, Pseudomonas fluorescens, Pseudomonas lutea, Pseudomonas poae, Pseudomonas putida, Pseudomonas stutzeri, Pseudomonas trivialis, Serratia marcescens, Stenotrophomonas maltophilia, Streptotmyces* spp., *Streptosporangium* spp., *Swaminathania salitolerans, Thiobacillus ferrooxidans, Torulospora globosa, Vibrio proteolyticus, Xanthobacter agilis,* and *Xanthomonas campestris.*

In another embodiment, the present invent on includes a method of enhancing plant growth, comprising applying to plants, plant seeds, or soil surrounding plants, or plant seeds one or more of the bacterial strain(s) of the present invention (including a composition comprising at least one of the isolated bacterial strain(s) of the present invention and an agronomically acceptable carrier. The one or more bacterial strains may comprise only one bacterial strain or a combination of at least two or more of the strains of the present invention, including more than two, such as, at least three of the above strains, at least four of the above strains, at least five of the above strains, at least six of the above strains, at least seven of the above strains, at least eight of the above strains, at least nine of the above strains, at least ten of the above strains, at least eleven of the above strains, at least twelve of the above strains, at least thirteen of the above strains, up to an including all of the above strains.

Applications

Methods of the invention include a treatment step for applying at least one of the isolated strains and/or compositions comprising at least one of the isolated strains to seeds, seedlings, roots, plants, soils, or combinations thereof. "Treating" or "treatment," as the terms are used herein and in the art, refers to any application which results in contact of seeds, seedlings, roots, or plants with an effective amount of a treatment composition or components to enhance competitiveness for colonizing a plant and effectiveness at promoting plant growth.

The effective amount and/or suitable application rates vary according to the type of soil, the type of plants, the amounts of the source of micronutrients present in the soil or added thereto, etc. and a suitable rate can be found without difficulty by simple trial and error experiments for each particular case. Normally, the rate for applying at least one of the isolated strains and/or compositions comprising at least one of the isolated strains falls into the range of $1 \times 10^2$-$1 \times 10^8$ colony forming units (cfu) per seed (when coated seeds are used). In a specific embodiment, the application rate falls in the range of $1 \times 10^4$-$1 \times 10^5$ colony forming units (cfu) per seed (when coated seeds are used. On a granular carrier, the application rate falls into the range of $1 \times 10^8$-$1 \times 10^{13}$ cfu per hectare. In a specific embodiment, the application rate on a granular carrier falls into the range of $2 \times 10^{11}$-$6 \times 10^{11}$ cfu per hectare. Even though the inoculant compositions and/or compositions used according to the present invention may include a mixture/combination of at least two or more different bacterial strains, it is the total amount of colony forming units in the combined mixture that is referred to throughout the specification. The effective amount of LCO and/or CO used in a composition of the invention for treating a seed directly is expressed in units of concentration and generally ranges from about $10^{-5}$ to about $10^{-14}$ M (molar concentration), and in some embodiments, from about $10^{-5}$ to about $10^{-14}$ M, and in some other embodiments from about $10^{-7}$ to about $10^{-8}$ M. Expressed in units of weight, the effective amount generally ranges from about 1 to about 400 µg/hundred weight (cwt) seed, and in some embodiments from about 2 to about 70 µg/cwt, and in some other embodiments, from about 2.5 to about 3.0 µg/cwt seed.

For purposes of treatment of seed indirectly, i.e., in-furrow treatment, the effective amount of the LCO or CO generally ranges from 1 µg/acre to about 70 µg/acre, and in some embodiments, from about 50 µg/acre to about 60 µg/acre. For purposes of application to the plants, the effective amount of the LCO or CO generally ranges from 1 µg/acre to about 30 µg/acre, and in some embodiments, from about 11 µg/acre, to about 20 µg/acre.

Treatment may be accomplished directly. i.e., by application directly on seeds, seedlings, roots, or plants (including foliage), or may be accomplished indirectly, i.e., by application to the soil (including in furrow).

As will be understood, treatment with each component may be accomplished sequentially or simultaneously. For example, if a liquid carrier is used, the components may be co-slurried in a commercial treater mix tank and subsequently applied to seeds by any suitable coating process, e.g., film coating. In the film coating process, a slurry is sprayed onto the seeds in a continuous coating process. Alternatively, for example, if a dust or powder carrier is used, the components can be sequentially applied. Accordingly, treatment may also encompass foliar application and/or application of the compositions in furrow.

Non-limiting examples of plants to be treated by the isolated strains and/or compositions comprising at least one of the isolated strains include leguminous crops. Non-limiting examples of leguminous crops include, but are not limited to, plants such as soybean, alfalfa, peanut, pea, lentil, bean, and clover. As will be appreciated, the term "crop" encompasses any plant material that may be harvested.

Culture

The present invention is directed to a biologically pure culture of *Bradyrhizobia japonicum* strain(s)

the strain having the deposit accession number NRRL B-50592 (deposited also as NRRL B-59571);
the strain having the deposit accession number NRRL B-50593 (deposited also as NRRL B-59572);
the strain having the deposit accession number NRRL B-50586 (deposited also as NRRL B-59565);
the strain having the deposit accession number NRRL B-50588 (deposited also as NRRL B-59567);
the strain having the deposit accession number NRRL B-50587 (deposited also as NRRL B-59566);
the strain having the deposit accession number NRRL B-50589 (deposited also as NRRL B-59568);
the strain having the deposit accession number NRRL B-50591 (deposited also as NRRL B-59570);
the strain having the deposit accession number NRRL B-50590 (deposited also as NRRL B-59569);
the strain having the deposit accession number NRRL B-50594 (deposited also as NRRL B-50493);
the strain having the deposit accession number NRRL B-50726;
the strain having the deposit accession number NRRL B-50727;
the strain having the deposit accession number NRRL B-50728;
the strain having the deposit accession number NRRL B-50729; and
the strain having the deposit accession number NRRL B-50730.

As used herein, the phrase "biologically pure culture" means a culture essentially free from biological contamination and having a genetic uniformity such that different subcultures taken therefrom will display substantially identical genotypes and phenotypes (e.g., cultures have a purity of at least 60%, of at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, up to 100% pure). Such cultures may be useful in large-scale fermentation or for other commercial purposes. Accordingly, mutants, transconjugants, recombinants, and genetically engineered variants which are derived from *Bradyrhizobium japonicum* strains having the deposit accession numbers NRRL B-50592 (deposited also as NRRL B-59571), NRRL B-50593 (deposited also as NRRL B-59572), NRRL B-50586 (deposited also as NRRL B-59565), NRRL B-50588 (deposited also as NRRL B-59567), NRRL B-50587 (deposited also as NRRL B-59566), NRRL B-50589 (deposited also as NRRL B-59568), NRRL B-50591 (deposited also as NRRL B-59570); NRRL B-50590 (deposited also as NRRL B-59569); NRRL B-50594 (deposited also as NRRL B-50493); NRRL B-50726; NRRL B-50727; NRRL B-50728; NRRL B-50729; NRRL B-50730, and cultures thereof are within the scope of the invention.

In one embodiment the culture is a strain having the deposit accession number NRRL B-50592 (deposited also as NRRL B-59571). In another embodiment the culture is a strain having the deposit accession number NRRL B-50593 (deposited also as NRRL B-59572). In another embodiment the culture is a strain having the deposit accession number NRRL B-50586 (deposited also as NRRL B-59565). In another embodiment the culture is a strain having the deposit accession number NRRL B-50588 (deposited also as NRRL B-59567). In another embodiment the culture is a strain having the deposit accession number NRRL B-50587 (deposited also as NRRL B-59566). In another embodiment the culture is a strain having the deposit accession number NRRL B-50589 (deposited also as NRRL B-59568). In another embodiment the culture is a strain having the deposit accession number NRRL B-50591 (deposited also as NRRL B-59570). In another embodiment the culture is a strain having the deposit accession number NRRL B-50590 (deposited also as NRRL B-59569). In another embodiment the culture is a strain having the deposit accession number NRRL B-50594 (deposited also as NRRL B-50493). In another embodiment the culture is a strain having the deposit accession number NRRL B-50726. In another embodiment the culture is a strain having the deposit accession number NRRL B-50727. In another embodiment the culture is a strain having the deposit accession number NRRL B-50728. In another embodiment the culture is a strain having the deposit accession number NRRL B-50729. In another embodiment the culture is a strain having the deposit accession number NRRL B-50730.

Deposit of Biological Material

The following biological material has been deposited under the terms of the Budapest Treaty at American Type Culture Collection (ATCC), 10801 University Blvd., Manassas, Va. 20108, USA, and the Microbial Genomics and Bioprocessing Research Unit (NRRL) National Center for Agricultural Utilization Research 1815 N. University Street, Peoria, Ill. 61604, USA and given the following accession number:

TABLE 1

Deposit of Biological Material

| Identification | Accession Number | Date of Deposit |
|---|---|---|
| *Bradyrhizobia japonicum* | NRRL B-50592 | Nov. 09, 2011 |
| | NRRL B-59571 | Mar. 08, 2011 |
| *Bradyrhizobia japonicum* | NRRL B-50593 | Nov. 09, 2011 |
| | NRRL B-59572 | Mar. 08, 2011 |
| *Bradyrhizobia japonicum* | NRRL B-50586 | Nov. 09, 2011 |
| | NRRL B-59565 | Mar. 08, 2011 |

TABLE 1-continued

Deposit of Biological Material

| Identification | Accession Number | Date of Deposit |
|---|---|---|
| Bradyrhizobia japonicum | NRRL B-50588 | Nov. 09, 2011 |
|  | NRRL B-59567 | Mar. 08, 2011 |
| Bradyrhizobia japonicum | NRRL B-50587 | Nov. 09, 2011 |
|  | NRRL B-59566 | Mar. 08, 2011 |
| Bradyrhizobia japonicum | NRRL B-50589 | Nov. 09, 2011 |
|  | NRRL B-59568 | Mar. 08, 2011 |
| Bradyrhizobia japonicum | NRRL B-50591 | Nov. 09, 2011 |
|  | NRRL B-59570 | Mar. 08, 2011 |
| Bradyrhizobia japonicum | NRRL B-50590 | Nov. 09, 2011 |
|  | NRRL B-59569 | Mar. 08, 2011 |
| Bradyrhizobia japonicum | NRRL B-50594 | Nov. 09, 2011 |
|  | NRRL B-50493 | Mar. 08, 2011 |
| Bradyrhizobia japonicum | NRRL B-50726 | Mar. 09, 2012 |
| Bradyrhizobia japonicum | NRRL B-50727 | Mar. 09, 2012 |
| Bradyrhizobia japonicum | NRRL B-50728 | Mar. 09, 2012 |
| Bradyrhizobia japonicum | NRRL B-50729 | Mar. 09, 2012 |
| Bradyrhizobia japonicum | NRRL B-50730 | Mar. 09, 2012 |

*NRRL indicates deposit with the Agricultural Research Service Culture Collection, Peoria, IL.

The strain has been deposited under conditions that assure that access to the culture will be available, during the pendency of this patent application to one determined by the Commissioner of Patents and Trademarks to be entitled thereto under 37 C.F.R. §1.14 and 35 U.S.C. §122. The deposit represents a pure culture of the deposited strain. The deposit is available as required by foreign patent laws in countries wherein counterparts of the subject application or its progeny are filed. However, it should be understood that the availability of a deposit does not constitute a license to practice the subject invention in derogation of patent rights granted by governmental action.

The following examples are included for illustrative purposes only and are not intended to limit the scope of the invention.

EXAMPLES

Materials and Methods

Media

YEM Agar (YEMA): (10 g/L D-mannitol; 0.50 g/L Oxoid yeast extract; 0.10 g/L NaCl; 0.50 g/L $K_2HPO_4$; 0.20 g/L $MgSO_4.7H_2O$; 12.0 g/L Agar; pH≈6.8)

Liquid YEM: (10 g/L D-mannitol; 0.50 g/L. Oxoid yeast extract; 0.10 g/L NaCl; 0.50 g/L $K_2HPO_4$; 0.20 g/L $MgSO_4.7H_2O$; pH≈6.8).

DNA Isolation Protocol

For strains grown on plates, a 1 µL loop of each strain from plates was added individually to 100 µL PrepMan® Ultra DNA Isolation solution from Applied Biosystems. The solution was heated to 100° C. for 10 minutes. Isolated DNA was used for PCR analysis.

For DNA isolated from nodules, nodules were removed with forceps from soybean roots and rinsed in $diH_2O$. Nodules were placed individually in 100 µL PrepMan® Ultra DNA Isolation solution from Applied Biosystems, broken apart, and heated at 100° C. for 10 minutes using a 96-well PCR Plate also from Applied Biosystems. Disposable toothpicks were used to break the nodules open to avoid cross contamination. Isolated DNA was used for PCR analysis.

PCR Protocol

Polymerase chain reactions (PCR) were performed using Applied Biosystems Veriti® 96-well Fast Thermal Cycler. PCRs were set up for each strain. 2 µL of DNA was added to 0.5 µL of a 3' primer, 0.5 µL of a 5' primer, 0.5 µL of Taq Polymerase (New England Biolabs, Inc.) and 21.5 µL Platinum Blue PCR Supermix® (Invitrogen). The PCR mixture was heated to 94° C. for 4 minutes, Following denaturation, the PCR was performed for 35 cycles with the following program: 94° C. for 1 minute, 68° C. or primer annealing dependent temperature(s) for 1 minute, and reaction extension at 72° C. for 1 minute. After completion of the PCR program, 5 µL of PCR mixture was run on a Lonza® FlashGel® system.

Strain Isolation Protocol

To isolate strains, nodules were surface sterilized with 10% household bleach for 2 minutes. Nodules were rinsed in sterile water and then placed in a microcentrifuge tube with 250 µL of sterile water. Nodules were crushed with sterile toothpicks and the Rhizobium strains were released into the water. Two 10 µL loops of water were streaked out for single colonies onto YEMA plates. All plates were wrapped with Parafilm® and grown at 30° C. in an Eppendorf Innova® 42R incubator. Growing time differed per isolate.

Primary Screening Protocol

Strains were primarily screened by two distinct protocols, i.e., the "Soybean Field Soil Protocol (USDA 532C Treated Field)" and the "Untreated (Control) Field Protocol." Each protocol is described.

Soybean Field Soil Protocol (USDA 532C Treated Field)

Soybean seeds coated with USDA 532C were planted in various soils throughout soybean growing regions in the United States, e.g., South Dakota, North Dakota, Georgia, Iowa, Nebraska, Illinois, Indiana, Texas, Kansas, Minnesota, etc., Soybean seeds treated with Bradyrhizobium japonicum strain USDA 532C were grown in these soils, harvested, and the soybean nodules were analyzed directly using PCR analysis, Forty (40) nodules were collected from each soil sample. Individual soybean nodules were loaded into a single well of 96 well microtiter plate. DNA from those individual soybean nodules was isolated directly from nodules based on the procedure described supra (see Materials and Methods: DNA Isolation Protocol).

PCR analysis using USDA 532C specific primer 209 was performed directly on the 96 well plate (see Materials and Methods: PCR Protocol). The amplification of primer 209 (0.9 kb band) from the 40 nodules was calculated to determine the percent amplification. If the 0.9 kb DNA amplification was less than or equal to 30% (i.e., greater than or equal to 70% of the PCR was negative for primer 209 amplification), then the soil sample contained Bradyrhizobium japonicum strains with greater competitiveness than the USDA 532C strain. Soybean nodules with less than or equal to 30% amplification contained native strains identified as being more competitive than USDA 532C based on the procedure described (see Materials and Methods: Strain Isolation Protocol).

If more than 30% of soybean nodules were colonized by Bradyrhizobia japonicum strain USDA 532C, then the soil was deemed unfit for novel strain isolation and the soil sample was terminated.

Untreated Field (Control) Protocol

Nodules were obtained from soybean fields untreated with USDA 532C, in the following states: Arkansas, Georgia, Illinois, Indiana, Iowa, Oklahoma, Nebraska, Kansas, Missouri, and Texas. Bradyrhizobium japonicum strains were isolated directly from these nodules per the protocol described supra (see Materials and Methods: Strain Isolation Protocol). Isolated strains were put into direct competition with Bradyrhizobia japonicum strain USDA 532C per the "Competition Study Protocol" (see Materials and Methods: Competition Study Protocol). Isolated strains that occupied more than 70% of soybean nodules when compared to *Bradyrhizobia japonicum* strain USDA 532C, were selected for performance evaluation (see Materials and Methods: Performance Study Protocol).

Competition Study Protocol

Optical densities were determined. (Nanodrop® ND1000 Spectrophotometer) A 1:1 inoculum ratio of USDA 532C to each isolate strain was obtained, USDA 532C was diluted or concentrated to an optical density of 0.5 at 600 nm and 0.5 mL of USDA 532C inoculum was set aside for each isolate. All isolate strains were either concentrated or diluted to an optical density of 0.5 at 600 nm using the following calculation: (0.5 optical density USDA 532C)=(0.5 mL USDA 532C)=(isolate strain optical density)×(isolate strain mL). 0.5 mL. of USDA 532C was added to 0.5 mL of each isolate as separate treatments. Soybean seeds were coated with the inoculum mixture at a rate of 0.5 mL inoculum mixture per 12 soybean seeds. The seeds were allowed to imbibe for 30 minutes. 5 of the 12 treated soybean seeds were planted in Fafard® 3B Potting mix in a 1 gallon pot. Gloves were worn to plant the seeds and were changed between treatments. Following planting, the 7 remaining treated soybean seeds were discarded.

At germination, pots were thinned to 3 plants. Plants were grown for 6-7 weeks in a greenhouse and cross-contamination during the watering process was avoided. Temperatures ranged from approximately 23° C.-32° C. Watering was performed on an "as needed" basis. Nodules were harvested from each treatment and used for DNA isolation and PCR analysis with USDA 532C specific primer 209. See Materials and Methods: DNA isolation protocol and POR Protocol.

Performance Study Protocol

The performance study is a direct strain to strain performance comparison between a single isolated strain and commercially available *Bradyrhizobium japonicum* strain USDA 532C. The isolate strain and the control strain (*Bradyrhizobium japonicum* strain USDA 532C) were streaked out concurrently on separate YEMA plates, The isolate strain and the control strain were separately inoculated into 5 mL of YEM liquid media to obtain an initial optical density of 0.03 at 600 nm in each inoculum tube, (Nanodrop® ND1000 Spectrophotometer) The isolate strain and the control strain were incubated separately at 30° C. for 3 days. Following incubation, the inoculum for the isolate strain and the control strain was further diluted or concentrated to a final optical density of 0.5 at 600 nm in each inoculum tube (Nanodrop® ND1000 Spectrophotometer) to obtain a test treatment (isolate strain) and a control treatment (control strain *Bradyrhizobium japonicum* strain USDA 532C).

0.75 mL of the test treatment was added to 32 soybean seeds. The treated seeds were allowed to imbibe for 30 minutes. After 30 minutes, 2 seeds were planted into 15 separate (4"×4"×6") pots in Fafard® 3B Potting mix. Gloves were worn to plant the seeds and were changed between treatments. Following planting, the 2 remaining treated soybean seeds were discarded, This process was repeated for the control treatment.

At germination, test treatment and control treatment pots were thinned to a single plant. Plants were grown for 8-10 weeks in a greenhouse and cross-contamination during the watering process was avoided. Temperatures ranged from approximately 23° C.-32° C. Watering was performed on an "as needed" basis. After 8-10 weeks, pods were harvested and dried overnight at 80° C. Analysis with JMP® statistical software (SAS Institute, Inc.) was used to determine statistically significant performance enhancement compared to *Bradyrhizobium japonicum* strain USDA 532C.

Temperature Profile Protocol

Isolated *Bradyrhizobium japonicum* strains were streaked onto YEMA plates (10 g/L D-mannitol; 0.50 g/L Oxoid yeast extract; 0.10 g/L NaCl; 0.50 g/L $K_2HPO_4$; 0.20 g/L $MgSO_4.7H_2O$; 12.0 g/L Agar; pH≈6.8) and incubated at 30° C. and 35° C. respectively for 7 days. The isolated strains were analyzed for their ability to grow isolated colonies.

Glyphosate Resistance Profile Protocol

Isolated *Bradyrhizobium japonicum* strains were streaked onto 1 mM glyphosate, and 2 mM glyphosate. YEMA plates (10 g/L D-mannitol; 0.50 g/L Oxoid yeast extract; 0.10 g/L NaCl; 0.50 g/L $K_2HPO_4$; 0.20 g/L $MgSO_4.7H_2O$; 12.0 g/L Agar; pH≈6.8). The plates were incubated at 30° C. for 7 days and the strains were analyzed for their ability to grow isolated colonies.

Antibiotic Profile Protocol

Isolated *Bradyrhizobium japonicum* strains were T-streaked onto gentamicin (50 mg/L) YEMA, chloramphenicol (50 mg/L) YEMA, polymyxin B (100 mg/L) YEMA, carbenicillin (100 mg/L) YEMA, neomycin (50 mg/L) YEMA, and nalidixic acid (50 mg/L) YEMA. The plates were incubated at 30° C. for 7 days and the strains were analyzed for their ability to grow isolated colonies.

Diversilab® PCR Protocol

Diversilab® PCR was net up using the Diversilab Pseudomonas Kit® from BioMerieux. This kit contained proprietary primers designed to amplify various portions of the genome produce a fingerprint of multiple DNA amplifications. Each strain has a unique fingerprint and percent similarity among strains can be determined using the Diverilab software.

The PCR was setup accordingly. 2 µL of DNA was added to 18.0 µL of Re-PCR MM1, 2.0 µL of primer mix, 0.5 µL of Tag Polymerase (New England Biolabs, Inc.) and 2.5 µL of Tag Polymerase buffer (New England Biolabs, Inc.) for a total volume of 25 µL. The PCR was heated to 94° C. for 2 minutes and then run for 35 cycles according to the following: 94° C. for 0.5 minutes, then 50° C. for 0.5 minutes, and finally 70° C. for 1.5 minutes. After the completion of the 35 cycles, the entire reaction was maintained at 70° C. for 3 minutes. Following completion of the PCR analysis, the PCR product was run on the Agilent® 2100 Series Bioanalyzer. Diversilab® DNA Reagents & Supplies Kit from BioMerieux was used to load PCR product onto Diversilab® System chips. The kit was maintained according to instructions. Before use, the kit sat at room temperature for 30 minutes prior to loading the Diversilab® chip. The Diversilab® chip was loaded in full accordance with all protocols and instructions provided. Upon completion of loading the Diversilab® chip, the chip was loaded into the Agilent® 2100 Series Bioanalyzer and the analysis performed until completion.

Example 1

Unique Primer Design for Commercial *Bradyrhizobium* strain USDA 532C

A genetic identification method was developed to evaluate the competitiveness of commercial *Bradyrhizobium japonicum* strain USDA 532C against native strains in the field. A primer specific to USDA 532C was identified and PCR technology was used to efficiently evaluate competitiveness of USDA 532C in the field.

Complete genome sequencing of USDA 532C was performed at Novozymes Davis. Twenty-five different DNA fragments were found to have low homology with public sequences of *Bradyrhizobium japonicum*. DNA was isolated from strains of *B. japonicum* (USDA 532C, P152, Br173, Br187, P190, and P194) grown on plates according to the procedure described supra (see Materials and Methods: DNA Isolation Protocol). Additional sequence analysis was performed on those twenty-five DNA fragments. Putative unique primers for USDA 532C strain were chosen and used for USDA 532C-specific primer screening by PCR against some representative *Bradyrhizobium japonicum* strains. After PCR evaluation, a single unique primer for USDA 532C was identified and was designated as p209.

Primer 209 sequence was as follows:

```
                                      SEQ ID NO: 1
       P209p5-TTGGGTTGAGCATGCCCACCCGGACGG,

SEQ ID NO: 2
       P209p3-GTCTCAGTTGCCGAGCCCACGGCGC
```

Primer Specificity

The twenty-five primers were individually tested for positive identification of USDA 532C. The primers were further tested for USDA 532C specificity through FOR using USDA 532C and 5 different native strains of B. japonicum (P152, Br173, Br187, P190, and P194) for comparison. Genome sequencing indicated that Br187 and USDA 532C were genetically the same.

TABLE 2

Primer Screening Summary

| Primer | USDA 532C | P152 | Br173 | Br187 | P190 | P194 | PCR Temp |
|---|---|---|---|---|---|---|---|
| 787 | − | − | − | − | − | − | 65 |
| 1114 | + | + | + | + | + | + | 65 |
| 1181 | + | + | + | + | + | + | 64 |
| 943 | + | + | + | + | + | + | 60 |
| 1073 | + | + | + | + | + | + | 65 |
| 125 | + | − | − | + | − | − | 68 |
| 209* | + | − | − | + | − | − | 68 |
| 487 | + | − | − | + | − | − | 68 |
| 567 | + | − | − | + | − | − | 58 |
| 744 | + | − | − | + | − | − | 65 |
| 811 | + | − | − | + | − | − | 65 |
| 989 | + | − | − | + | − | − | 69 |
| 1073 | + | − | − | + | − | − | 69 |
| 989 a | + | − | − | + | − | − | 64 |
| 893 | + | − | − | + | − | − | 64 |
| 2254 | + | − | − | + | + | + | 68 |
| 607 | + | − | − | + | + | + | 68 |
| 389 | + | − | − | + | + | + | 60 |
| 728 | + | − | − | + | + | + | 65 |
| 869 | + | − | − | + | + | + | 62 |
| 1424 | + | − | + | + | + | + | 65 |
| 1181 | + | + | + | + | + | + | 60 |
| 989 b | + | − | + | + | + | + | 65 |
| 895 | + | − | + | + | + | + | 65 |
| 943 | + | − | − | + | + | − | 64 |

*Primer 209 exhibited the clearest bands and was chosen for further evaluation.

Table 2 summarizes the findings ("+" indicates a positive identification of a FOR amplification band in the gel, "−" indicates no DNA amplification).

Referring to FIG. 1A, it was demonstrated that isolated primer 209 is specific to USDA 532C and Br187. Further genetic testing, showed that USDA 532C and *Bradyrhizobium japonicum* strain P187 are identical (results not shown). The well contents (left to right) indicate the following native strains USDA 532C, P152, Br173, Br187, Br190, Br194, and the control ladder. See FIG. 1A.

Figure 1B:
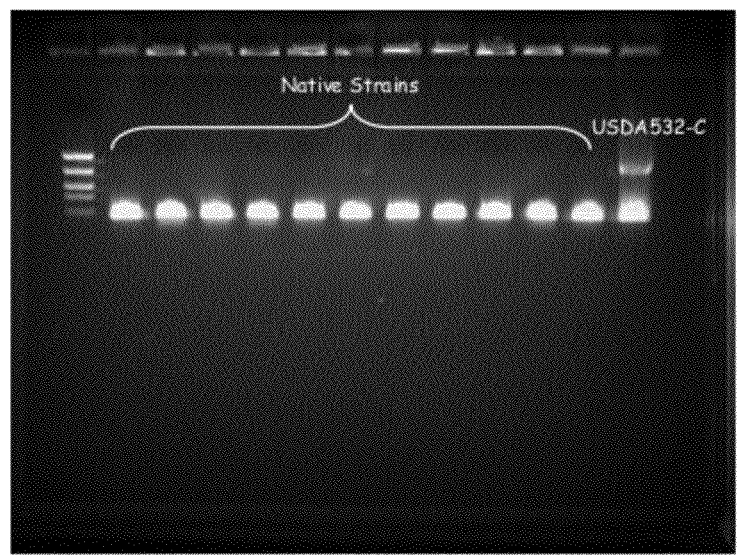
FIG. 1B is an image of a PCR gel showing Primer 209 specificity using USDA 532C and native strains.

The specificity of primer 209 was tested against native strains P152, Br173, Br187, Br190, Br194, and USDA 532C. See FIG. 1B. PCR with primer 209 was performed for 100 strains obtained from untreated plots in field trials according to the above method (see Materials and Methods: Untreated (Control) Field Protocol). *Bradyrhizobium japonicum* strain USDA 532C was not added to these plots. Of the strains tested, only 3% of the native strains could be amplified for a 0.9 kb band specific to primer 209. This result demonstrated that primer 209 could be used for specific detection of USDA 532C.

Example 2

Analyzing and Isolating Novel Strains

Figure 2A:
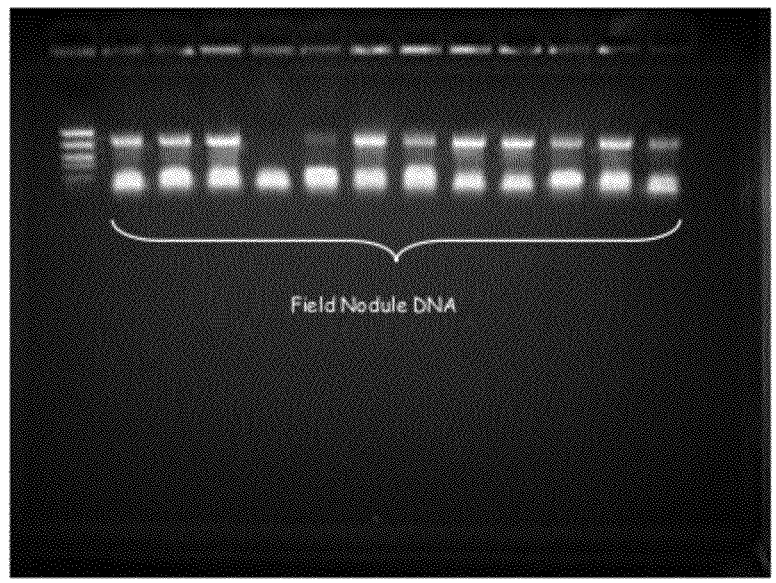
FIG. 2A is an image of a PCR gel showing *Bradyrhizobia japonicum* strain USDA 532C as the competitively dominant strain for soybean nodulation.
Figure 2B:
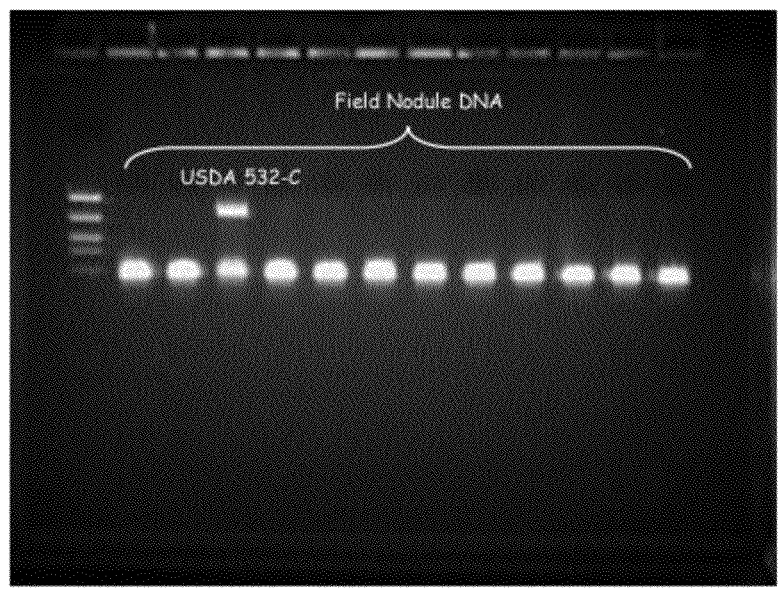
FIG. 2B is an image of a PCR gel showing strains other than *Bradyrhizobia japonicum* strain USDA 532C as the competitively dominant strain for soybean nodulation.

Primer 209 was used as a marker to indicate the presence or absence of colonization by *Bradyrhizobia japonicum* strain USDA 532C into the root nodules of soybean plants. Bands (i.e., a 0.9 kb band) indicating the presence of primer 209 represent a positive identification of *Bradyrhizobia japonicum* strain USDA 532C. See FIG. 2A. FIG. 2A is exemplary of an instance wherein *Bradyrhizobia japonicum* strain USDA 532C is the dominantly competitive strain for colonization of soybean plant nodules when compared to other native *Rhizobial* strains. In FIG. 2B, the number of bands indicating positive identification for primer 209, and therefore the presence of *Bradyrhizobia japonicum* strain USDA 532C, are reduced in comparison to the total number bands present for primer 209 in FIG. 2A. FIG. 2A and FIG. 2B demonstrate that the presence or absence of primer 209 can be used to determine whether USDA 532C is the dominantly competitive strain in the nodules of a soybean plant.

Isolated *Bradyrhizobium japonicum* strains were selected from nodules according to both screening protocols (see Materials and Methods: Primary Screening Protocol). The selected strains were isolated from the nodules according to the isolation procedure (see Materials and Methods: Strain Isolation Protocol).

Example 3

Head-to-Head Competition Evaluation

All isolated strains were put into a screening program designed to directly challenge the competitiveness of the isolate against *Bradyrhizobium japonicum* strain USDA 532C in terms of nodule colonization ability (see Materials and Methods: Competition Study Protocol).

Isolated primer 209 specific to USDA 532C was used as a marker to indicate the presence or absence of colonization by *Bradyrhizobia japonicum* strain USDA 532C into the root nodules of soybean plants. Positive identification for primer 209 indicated the colonization of *Bradyrhizobia japonicum* strain USDA 532C into the root nodules of soybean plants. Conversely, the absence of bands indicating positive identification for primer 209 indicated colonization of a native strain into the root nodules of soybean plants other than *Bradyrhizobia japonicum* strain USDA 532C. Isolated strains that exhibited a greater than 70% colonization of the analyzed nodules were chosen for a second evaluation for confirmation. Strains were subject to at least two rounds of competition evaluation. Through this procedure, over 1000 isolates have been screened for enhanced competitiveness.

Example 4

Performance Evaluation

The performance study is a direct strain to strain comparison of isolated strains to USDA 532C. Enhanced performance was measured as a function of Pod Dry Weight (g). See Materials and Methods: Performance Study Protocol. Results are provided in Tables 3A-3D

TABLE 3A

| Enhanced Performance as a Function of Pod Dry Weight (g) | | |
|---|---|---|
| Strain | Percent Colonization | Pod dry weight (g) |
| NRRL B-59571 | 85 | 5.92 |
| NRRL B-59567 | 80 | 6.12 |
| NRRL B-59572 | 85 | 6.05 |
| NRRL B-59565 | 80 | 5.87 |
| USDA532-C | — | 5.72 |

The percent colonization was confirmed in triplicate studies and increased pod dry weight was confirmed in duplicate studies for all strains.

TABLE 3B

| Enhanced Performance as a Function of Pod Dry Weight (g) | | |
|---|---|---|
| Strain | Percent Colonization | Pod dry weight (g) |
| NRRL B-50493 | 75 | 4.86 |
| NRRL B-59570 | 80 | 5.30 |
| USDA532-C | — | 5.45 |

The percent colonization was confirmed in triplicate studies and increased pod dry weight was confirmed in duplicate studies for all strains.

TABLE 3C

| Enhanced Performance as a Function of Pod Dry Weight (g) | | |
|---|---|---|
| Strain | Percent Colonization | Pod dry weight (g) |
| NRRL B-59566 | 85 | 5.30 |
| NRRL B-59569 | 85 | 5.50 |
| NRRL B-59568 | 95 | 5.69 |
| USDA532-C | — | 4.69 |

The percent colonization was confirmed in triplicate studies and increased pod dry weight was confirmed in duplicate studies for all strains.

TABLE 3D

| Enhanced Performance as a Function of Pod Dry Weight (g) | | |
|---|---|---|
| Strain | Percent Colonization | Pod dry weight (g) |
| NRRL B-50726 | 95 | 5.79 |
| NRRL B-50727 | 85 | 5.02 |
| NRRL B-50728 | 83 | 5.78 |
| NRRL B-50729 | 83 | 5.94 |
| NRRL B-50730* | 90 | 5.94 |
| USDA532-C | — | 5.45 |

The percent colonization and increased pod dry weight were confirmed in duplicate studies for all strains except NRRL B-50730* which has only had one round of testing.

Commercially available strain USDA 532C was used as a control for each evaluation. Results of Tables 3A-3D indicate that all but one of the isolated strains had enhanced performance when compared to the control, USDA 532C.

Example 5

Characterization Study

Isolated *Bradyrhizobium japonicum* strains were further characterized based on temperature, glyphosate resistance, and antibiotic profiles (see Materials and Methods: Temperature Profile, Glyphosate Resistance Profile, and Antibiotic Profile Protocols). Results provided in Table 4.

TABLE 4

Characterization of Isolated Strains as a Function of Temperature Profile, Glyphosate Resistance, and Antibiotic Resistance

| Treatment | NRRL B-59565 | NRRL B-59572 | NRRL B-59567 | NRRL B-59566 | NRRL B-59570 | NRRL B-59568 | NRRL B-59569 | NRRL B-50493 | NRRL B-59571 | USDA 532C |
|---|---|---|---|---|---|---|---|---|---|---|
| 30° C. | + | + | + | + | + | + | + | + | + | + |
| 35° C. | + | − | − | + | + | + | − | + | − | − |
| 1.0 mM glyphosate | + | − | − | − | − | + | + | + | − | − |
| 2.0 mM glyphosate | − | − | − | − | +− | − | + | − | − | − |
| Gentamicin | + | − | − | − | + | − | + | +− | − | + |
| Chloramphenicol | + | − | − | + | + | + | + | + | − | + |
| Polymyxin B | + | + | + | + | + | + | + | + | + | + |
| Carbenicillin | + | − | − | − | − | − | + | − | +− | + |
| Neomycin | + | − | + | +− | − | + | + | − | + | + |
| Nalidixic acid | − | − | − | + | − | − | + | − | − | − |

Table 4 summarizes the results ("+" indicates growth with isolated colonies, "-" indicates no growth, and "+-" indicates a few isolated colonies/minimal and sporadic growth). Results indicate that strains NRRL B-59570, NRRL B-59568, NRRL B-59565, NRRL B-59566 and NRRL B-50493 are tolerant to temperatures of substantially 35° C. Results further indicate that isolated strains NRRL B-59569, NRRL B-59568, NRRL B-59565, and NRRL B-50493 are naturally resistant to glyphosate. Strains NRRL B-59566 and NRRL B-59569 were found to have resistance to nalidixic acid.

Example 5

DNA Fingerprint Development

Top performing isolates were put through DNA Diversilab® fingerprint analysis (see Materials and Methods: Diversilab® PCR Protocol). DNA was isolated from each strain according to the methods discussed (see Materials and Methods: DNA isolation Protocol). Isolated DNA was used for PCR analysis.

Figure 3A:
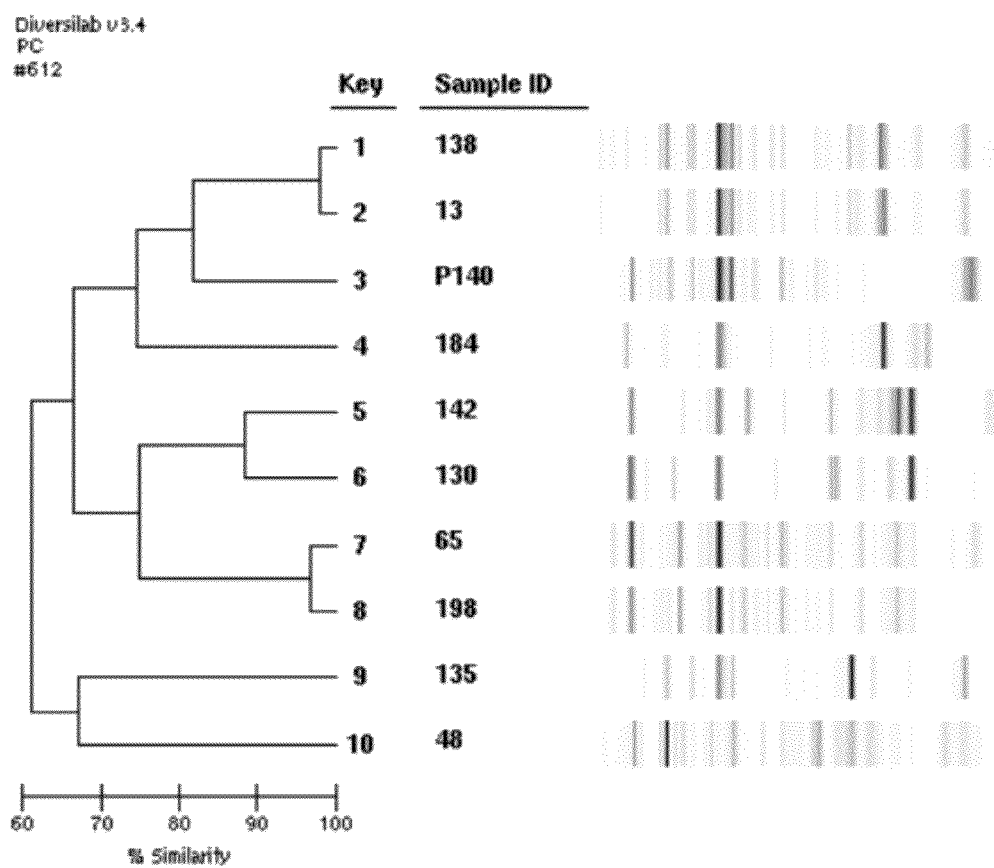
FIG. 3A is a DNA fingerprint dendrogram of isolated strains and USDA 532C:
138—NRRL B-50589 (deposited also as NRRL B-59568);
13—NRRL B-50586 (deposited also as NRRL B-59565);
p140—USDA 532C;
184—NRRL B-50594 (deposited also as NRRL B-50493);
142—NRRL B-50590 (deposited also as NRRL B-59569);
130—NRRL B-50587 (deposited also as NRRL B-59566);
65—NRRL B-50588 (deposited also as NRRL B-59567);
198—NRRL B-50592 (deposited also as NRRL B-59571);
135—NRRL B-50591 (deposited also as NRRL B-59570); and
48—NRRL B-50593 (deposited also as NRRL B-59572).
Figure 3B:
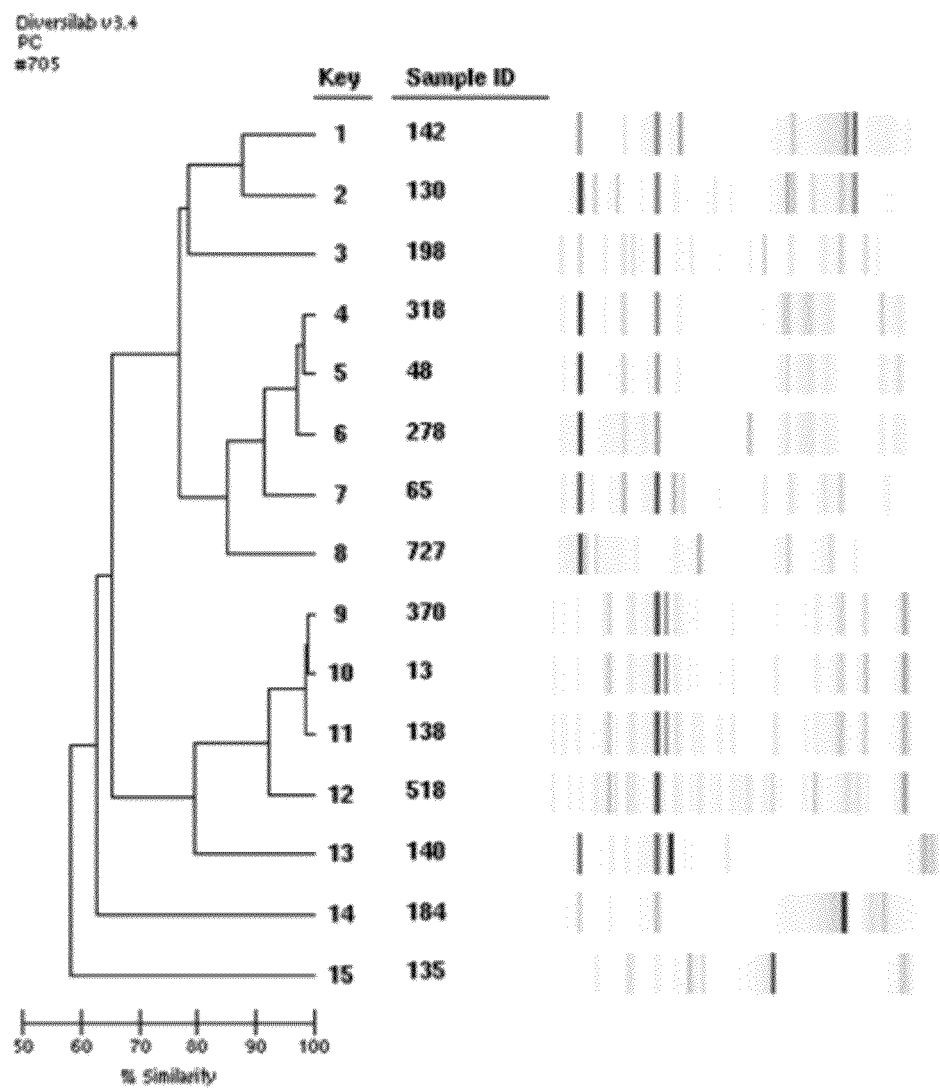
FIG. 3B is a DNA fingerprint dendrogram of isolated strains and USDA 532C:
138—NRRL B-50589 (deposited also as NRRL B-59568);
13—NRRL B-50586 (deposited also as NRRL B-59565);
140—USDA 532C;
184—NRRL B-50594 (deposited also as NRRL B-50493);
142—NRRL B-50590 (deposited also as NRRL B-59569);
130—NRRL B-50587 (deposited also as NRRL B-59566);
65—NRRL B-50588 (deposited also as NRRL B-59567);
198—NRRL B-50592 (deposited also as NRRL B-59571);
135—NRRL B-50591 (deposited also as NRRL B-59570);
48—NRRL B-50593 (deposited also as NRRL B-59572)
318—NRRL B-50727,
278—NRRL B-50726,
727—NRRL B-50730,
370—NRRL B-50728; and
518—NRRL B-50729.

Results to the Diversilab DNA Fingerprint Analysis are indicated in FIGS. 3A-3B, Results demonstrate that the isolated strains are unique strains and strains different than USDA 532C.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

The invention claimed is:

1. An inoculant composition suitable for coating seeds, said composition comprising an agronomic ally acceptable carrier, wherein the agronomically acceptable carrier comprises a peat-based powder or granule, and at least one biologically pure culture of *Bradyrhizobia japonicum* strain selected from the group consisting of:
   the strain having the deposit accession number NRRL B-50592;
   the strain having the deposit accession number NRRL B-50593;
   the strain having the deposit accession number NRRL B-50586;
   the strain having the deposit accession number NRRL B-50588;
   the strain having the deposit accession number NRRL B-50587;
   the strain having the deposit accession number NRRL B-50589;
   the strain having the deposit accession number NRRL B-50591;
   the strain having the deposit accession number NRRL B-50590;
   the strain having the deposit accession number NRRL B-50594;
   the strain having the deposit accession number NRRL B-50726;
   the strain having the deposit accession number NRRL B-50727;
   the strain having the deposit accession number NRRL B-50728;
   the strain having the deposit accession number NRRL B-50729; and
   the strain having the deposit accession number NRRL B-50730.

2. The inoculant composition of claim 1, wherein said at least one *Bradyrhizobia japonicum* strain is capable of promoting Nitrogen fixation in a plant.

3. The inoculant composition of claim 1, wherein said at least one *Bradyrhizobia japonicum* strain is tolerant to growth at a temperature of substantially 35° C.

SEQUENCE LISTING

<160> NUMBER OF SEQ ID NOS: 2

<210> SEQ ID NO 1
<211> LENGTH: 27
<212> TYPE: DNA
<213> ORGANISM: Artificial Sequence
<220> FEATURE:
<223> OTHER INFORMATION: Primer 209p5

<400> SEQUENCE: 1
ttgggttgag catgcccacc cggacgg                              27

<210> SEQ ID NO 2
<211> LENGTH: 25
<212> TYPE: DNA
<213> ORGANISM: Artificial Sequence
<220> FEATURE:
<223> OTHER INFORMATION: Primer 209p3

<400> SEQUENCE: 2
gtctcagttg ccgagcccac ggcgc                                25

4. The inoculant composition of 3, wherein said at least one *Bradyrhizobia japonicum* strain is selected from the group consisting of:
the strain having the deposit accession number NRRL B-50591;
the strain having the deposit accession number NRRL B-50589;
the strain having the deposit accession number NRRL B-50586; and
the strain having the deposit accession number NRRL B-50594.

5. The inoculant composition of claim 1, wherein said at least one *Bradyrhizobia japonicum* strain is naturally resistant to glyphosate.

6. The inoculant composition of claim 5, wherein said at least one *Bradyrhizobia japonicum* strain is selected from the group consisting of:
the strain having the deposit accession number NRRL B-50590; and
the strain having the deposit accession number NRRL B-50594.

7. The inoculant composition of claim 1, wherein said at least one *Bradyrhizobia japonicum* strain has enhanced competitiveness for colonizing a plant.

8. The inoculant composition of claim 1, wherein said at least one *Bradyrhizobia japonicum* strain has enhanced effectiveness at promoting plant growth.

9. The inoculant composition of claim 7, wherein enhanced competitiveness includes an at least 51% nodule occupancy, e.g., at least 55%, at least 60%, at least 65%, at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% nodule occupancy.

10. The inoculant composition of claim 8, wherein enhanced effectiveness includes at least one of increased plant yield measured in terms of bushels/acre, increased fruit number, increased root number, increased root length, increased root mass, increased root volume, increased leaf area, increased plant stand, increased plant vigour, and/or increased nitrogen ($N_2$) fixing capability when compared to a commercially available strain, e.g., USDA 532C.

11. The inoculant composition of claim 8, wherein said plant is soybean and wherein enhanced effectiveness includes an increase in the total dry weight of soybean pods on said soybean plant when said total dry weight of soybean pods is compared to the total dry weight of soybean pods on a soybean plant subjected to a commercially available strain, e.g., commercial strain USDA 532C.

12. The inoculant composition of claim 1, further comprising one or more isolated plant signal molecules.

13. The inoculant composition of claim 12, wherein said one or more isolated plant signal molecules comprises a lipo-chitooligosaccharide (LCO), a chitinous compound, a flavonoid, and/or a karrikin.

14. The inoculant composition of claim 12, wherein said one or more isolated plant signal molecules comprises jasmonic acid or an ester, amide, glycoside or salt thereof; linoleic acid or an ester, amide, glycoside or salt thereof; and/or linolenic acid or an ester, amide, glycoside or salt thereof.

15. The inoculant composition of claim 1, further comprising a lipo-chitooligosaccharide (LCO) obtained from a species of *Rhizobia* selected from the group consisting of *Bradyrhizobium* spp., *Rhizobium* spp., *Sinorhizobium* spp. and *Azorhizobium* spp.

16. The inoculant composition of claim 15, further comprising at least one phosphate solubilising microorganism.

17. The inoculant composition of claim 16, wherein said at least one phosphate solubilizing microorganism comprises a strain of *Penicillium*.

18. The inoculant composition of claim 16, wherein said at least one phosphate-solubilizing microorganism comprises a strain of *P. bilaiae*.

19. The inoculant composition of claim 16, wherein said at least one phosphate-solubilizing microorganism comprises a strain of *P. gaestrivorus*.

20. The inoculant composition of claim 16, wherein said phosphate solubilizing microorganism comprises a strain of *P. gaestrivorus* having the deposit accession number NRRL 50170 and/or one or more strains of *P. bilaiae* selected from the group consisting of the strain having the deposit accession number NRRL 50162, the strain having the deposit accession number NRRL 50169, the strain having the deposit accession number ATCC 20851, the strain having the deposit accession number ATCC 22348, and the strain having the deposit accession number ATCC 18309.

21. A coated seed characterized in that the coating comprises the inoculant composition of claim 1.

\* \* \* \* \*